(12) United States Patent
Sadrieh

(10) Patent No.: US 10,241,964 B2
(45) Date of Patent: Mar. 26, 2019

(54) SYSTEMS AND METHODS FOR OBTAINING CONSENT FROM A PATIENT

(71) Applicant: Evocentauri Inc., Studio City, CA (US)

(72) Inventor: Ali Sadrieh, Studio City, CA (US)

(73) Assignee: Evocentauri Inc., Studio City, CA (US)

( * ) Notice: Subject to any disclaimer, the term of this patent is extended or adjusted under 35 U.S.C. 154(b) by 698 days.

(21) Appl. No.: 14/338,007

(22) Filed: Jul. 22, 2014

(65) Prior Publication Data

US 2015/0032473 A1  Jan. 29, 2015

Related U.S. Application Data

(60) Provisional application No. 61/857,624, filed on Jul. 23, 2013.

(51) Int. Cl.
*G06Q 50/00* (2012.01)
*G06F 16/73* (2019.01)
(Continued)

(52) U.S. Cl.
CPC .............. *G06F 16/73* (2019.01); *G06F 19/00* (2013.01); *G16H 10/20* (2018.01); *G16H 10/60* (2018.01); *G16H 40/20* (2018.01)

(58) Field of Classification Search
CPC ........ G06Q 50/22; G06Q 50/24; G06Q 40/08; G06Q 10/10; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20;
(Continued)

(56) References Cited

U.S. PATENT DOCUMENTS

| | | | | |
|---|---|---|---|---|
| 4,422,105 | A | * 12/1983 | Rodesch | G09B 5/02 |
| | | | | 348/552 |
| 6,064,968 | A | * 5/2000 | Schanz | G06Q 50/18 |
| | | | | 705/2 |
| 2012/0150562 | A1 | * 6/2012 | Lerner | G06Q 50/22 |
| | | | | 705/2 |

* cited by examiner

*Primary Examiner* — Tran N Nguyen
(74) *Attorney, Agent, or Firm* — Knobbe Martens Olson & Bear LLP

(57) ABSTRACT

Systems and methods are provided that leverage computers, and specifically a network like the Internet, to provide understandable information to a patient and to obtain meaningful consent from the patient. In particular, the systems and methods described herein may integrate with an electronic medical records (EMR) system to provide information to a patient. Such information may include an explanation of a how a procedure or treatment may be performed, possible complications or side effects that may occur, what a patient should do pre-op, what a patient should do during the procedure or treatment, and/or what a patient should do or expect post-op.

19 Claims, 15 Drawing Sheets

(51) Int. Cl.
*G16H 10/20* (2018.01)
*G16H 10/60* (2018.01)
*G16H 40/20* (2018.01)
*G06F 19/00* (2018.01)
*G06Q 10/00* (2012.01)

(58) Field of Classification Search
CPC ........ G16H 70/14; G16H 70/60; G16H 80/00; A61N 1/08
See application file for complete search history.

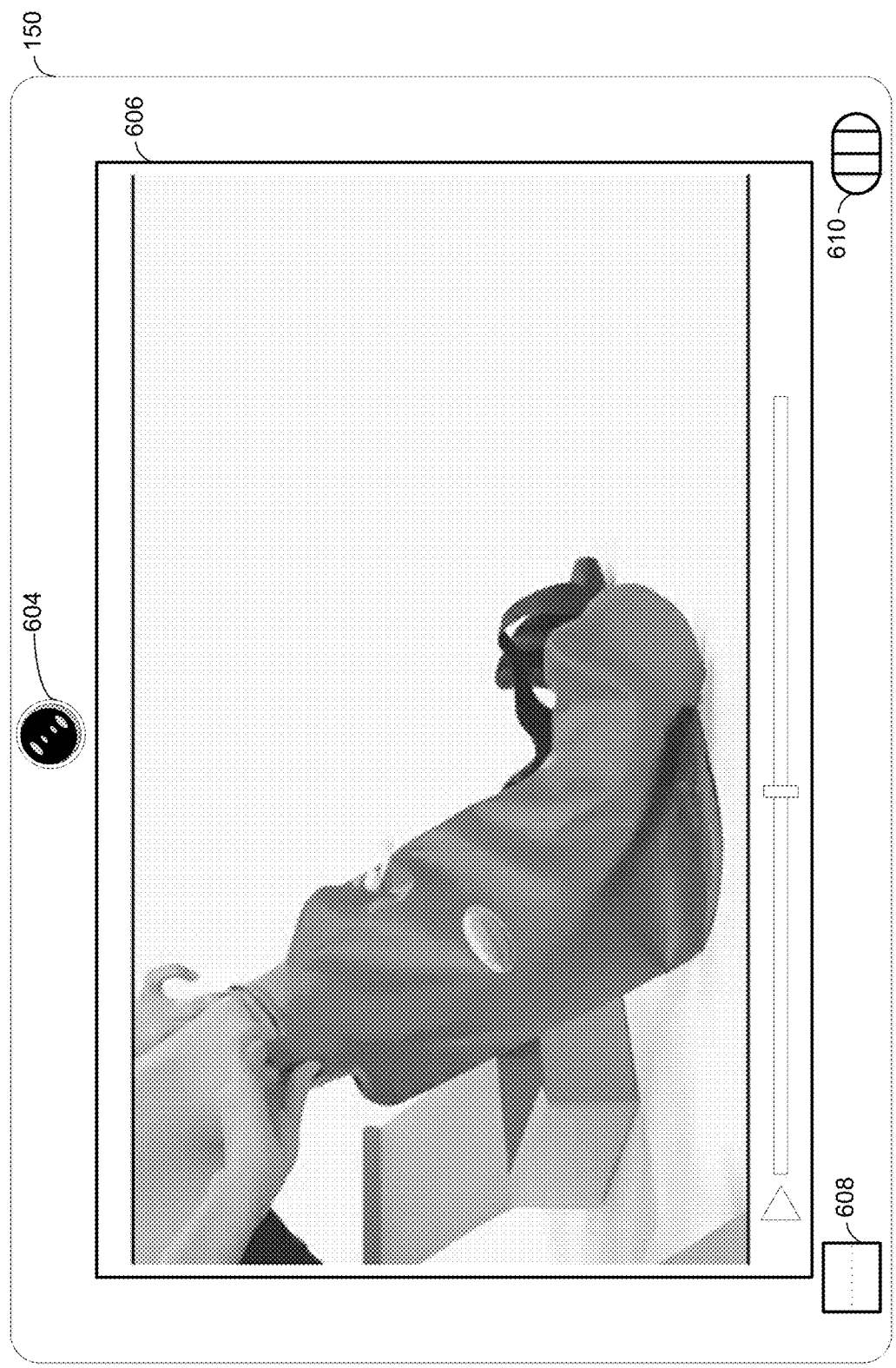

SYSTEMS AND METHODS FOR OBTAINING CONSENT FROM A PATIENT

RELATED APPLICATION

This application claims the benefit under 35 U.S.C. § 119(e) of U.S. Provisional Patent Application No. 61/857,624, filed on Jul. 23, 2013, and entitled "SYSTEMS AND METHODS FOR OBTAINING CONTENT FROM A PATIENT," the disclosure of which is hereby incorporated by reference in its entirety.

BACKGROUND

Field

This disclosure generally relates to communicating information to a user and more particularly to improved methods and systems for obtaining authorization from the user based on communicated information.

Description of the Related Art

Consent forms are used in a wide variety of fields, such as in construction, education, and medicine. While consent forms are generally prepared to provide laymen with important information, the forms are complicated, overly legalistic, and otherwise difficult to understand. In fact, often consent forms are signed without being reviewed or questioned. Ultimately, the party requesting execution of the consent form does not care whether or not the consent form is actually read and understood as long as a signature is present.

However, in certain fields, such as the medical field, it may be very important that the person executing the consent form understand the information provided in the form. For example, the form may set out the problem, the procedure or treatment, the post-operative care, and/or possible complications. Whether a patient understands such information may directly affect whether the patient can recover from whatever ails him or her. With the patient in mind, a consent form can be written like an instruction manual. For example, the consent form can be broken into sections to outline the problem, the procedure or treatment, the post-operative care, and/or possible complications, the consent form can include graphics and/or pictures to aid comprehension, and the content of the consent form can be written in conversational language.

While a consent form that breaks down aspects of a procedure or treatment and is written in a conversational tone may be more understandable, today, reading and writing in long-form is less prevalent due to the increased usage of computers and, in particular, the Internet. In fact, in part because of the Internet and its related applications, fewer people today have the attention span to read and comprehend such a consent form. Accordingly, what is needed is a system that can provide understandable information to a person and obtain meaningful consent from that person despite society's shorter attention span.

SUMMARY

A consent form, such as one that is used in the medical field, can be written to be more understandable by breaking down aspects of a procedure or treatment and by being written in a conversational tone. However, today, reading and writing in long-form is less prevalent due to the increased usage of computers and, in particular, the Internet. In fact, in part because of the Internet and its related applications, fewer people today have the attention span to read and comprehend consent forms, even if they are written to be more understandable. Usually, people do not read the consent forms; rather, they scroll or flip to the end of the document where a signature is requested and they sign the form. This can be problematic because, in the context of the medical field, once the procedure or treatment is complete, a patient may have complications and feel like he or she did not understand the consequences of the procedure or treatment. Even though the patient signed the consent form, there is no way of knowing whether the patient actually read and understood the consent form and the signature itself does not indicate that the patient actually read and understood the consent form.

Accordingly, as disclosed herein, systems and methods are provided that leverage computers, and specifically a network like the Internet, to provide understandable information to a patient and to obtain meaningful consent from the patient (e.g., consent is obtained from a patient once it is clear that the patient fully understands the content of the information that was provided). In particular, the systems and methods described herein may integrate with an electronic medical records (EMR) system to provide information to a patient. Such information may include an explanation of a how a procedure or treatment may be performed, possible complications or side effects that may occur, what a patient should do pre-op, what a patient should do during the procedure or treatment, and/or what a patient should do or expect post-op.

One aspect of the disclosure provides a computer-implemented method for constructing a non-linear video. The method comprises, as implemented by one or more computer systems comprising computer hardware and memory, the one or more computer systems configured with specific executable instructions, receiving, by the one or more computer systems, a diagnosis associated with a patient from an electronic medical records system. The method further comprises retrieving, by the one or more computer systems, a first video segment from a video database based on the received diagnosis, where the first video segment comprises first content associated with a first subject. The method further comprises generating, by the one or more computer systems, a first question based on an analysis of the first content, where the first question tests an ability of the patient to understand the first content. The method further comprises transmitting, by the one or more computer systems, the first video segment and data configured to cause a user device to display the first question to the user device over a network for presentation to the patient. The method further comprises receiving, by the one or more computer systems, a first answer from the user device over the network, where the first answer is selected by the patient in response to the first question. The method further comprises comparing, by the one or more computer systems, the first answer to an expected answer to the first question. The method further comprises retrieving, by the one or more computer systems, a second video segment from the video database in connection with a result of the comparison indicating that the first answer matches the expected answer, where the second video segment is retrieved based on the first answer and the diagnosis, and where the second video segment comprises second content associated with a second subject. The method further comprises retrieving, by the one or more computer systems, a third video segment from the video database in connection with a result of the comparison indicating that the first answer does not match the expected answer, where the third video segment is retrieved based on the first answer and the diagnosis, and where the third video segment comprises the first content and third content associated with the first subject. The method transmitting, by the one or more computer systems, the second video segment to the user device in connection with a result of the comparison indicating that the first answer matches the expected answer or the third video segment to the user device in connection with a result of the comparison indicating that the first answer does not match the expected answer for presentation to the patient.

Another aspect of the disclosure provides a computer-implemented method for obtaining consent from a patient. The method comprises, as implemented by one or more computer systems comprising computer hardware and memory, the one or more computer systems configured with specific executable instructions, receiving a diagnosis from an electronic medical records system, where the diagnosis is associated with a patient. The method further comprises generating a message based on the received diagnosis, where the message comprises a link to a video retrieved based on the received diagnosis. The method further comprises transmitting the message to the electronic medical records system. The method further comprises receiving a request to view the video from a user device, where the request is generated based on a selection of the link. The method further comprises transmitting the video to the user device in response to receiving the request. The method further comprises transmitting hardware instructions to the user device, where the hardware instructions comprise a request to provide a list of available hardware components. The method further comprises receiving, from the user device, the list of available hardware components. The method further comprises transmitting consent instructions to the user device, where the consent instructions comprise a request to obtain consent from the patient using a component in the list of available hardware components. The method further comprises receiving, from the user device, an indication that consent is obtained from the patient, where the user device obtains consent from the patient by activating the component in the list of available hardware components.

Another aspect of the disclosure provides a computing system configured to obtain consent from a patient. The computing system comprises a network interface coupled to a data network for receiving and transmitting one or more packet flows. The computing system further comprises a computer processor. The computing system further comprises a computer readable storage medium storing program instructions configured for execution by the computer processor in order to cause the computing system to receive a diagnosis from an electronic medical records system, where the diagnosis is associated with a patient; generate a message based on the received diagnosis, where the message comprises a link to a video retrieved based on the received diagnosis; transmit the message to the electronic medical records system; receive a request to view the video from a user device, wherein the request is generated based on a selection of the link; transmit the video to the user device in response to receiving the request; generate hardware instructions that are transmitted to the user device, where the hardware instructions comprise a request to provide a list of available hardware components; receive, from the user device, the list of available hardware components; transmit consent instructions to the user device, where the consent instructions comprise a request to obtain consent from the patient using a component in the list of available hardware components; and receive, from the user device, an indication that consent is obtained from the patient, where the user device obtains consent from the patient by activating the component in the list of available hardware components.

BRIEF DESCRIPTION OF THE DRAWINGS

Features and aspects, and advantages of the embodiments of the invention are described in detail below with reference to the drawings of various embodiments, which are intended to illustrate and not to limit the invention. The drawings include the following figures in which:

FIG. 6 is a diagram depicting an exemplary healthcare provider device and/or the one or more user devices of the communications system of FIG. 1.

DETAILED DESCRIPTION OF THE EMBODIMENT

Figure 1:
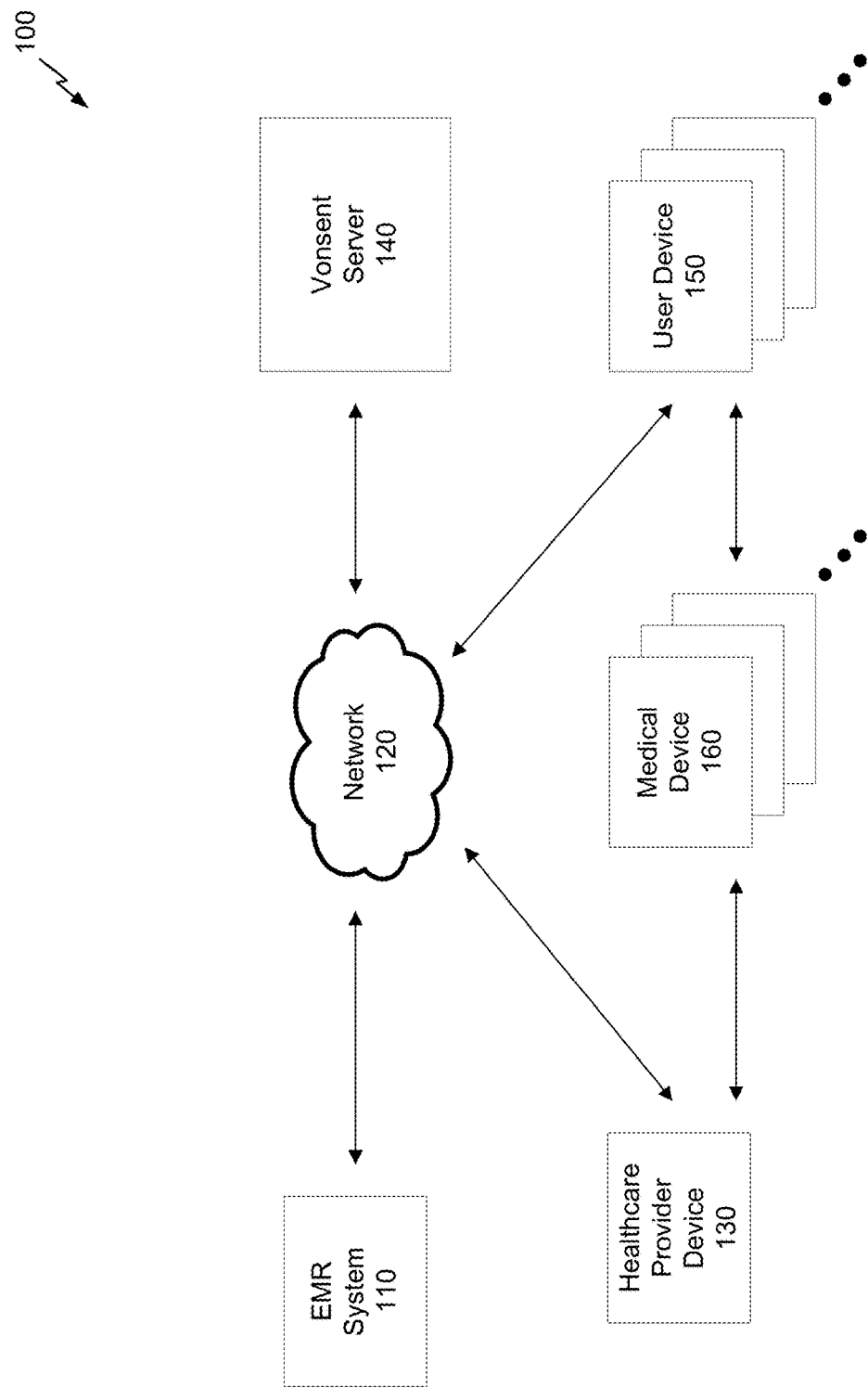
FIG. 1 is a block diagram depicting an exemplary communications system.

As described above, a consent form, such as one that is used in the medical field, can be written to be more understandable by breaking down aspects of a procedure or treatment and by being written in a conversational tone. However, today, reading and writing in long-form is less prevalent due to the increased usage of computers and, in particular, the Internet. In fact, in part because of the Internet and its related applications, fewer people today have the attention span to read and comprehend consent forms, even if they are written to be more understandable. Usually, people do not read the consent forms; rather, they scroll or flip to the end of the document where a signature is requested and they sign the form. This can be problematic because, in the context of the medical field, once the procedure or treatment is complete, a patient may have complications and feel like he or she did not understand the consequences of the procedure or treatment. Even though the patient signed the consent form, there is no way of knowing whether the patient actually read and understood the consent form and the signature itself does not indicate that the patient actually read and understood the consent form.

Accordingly, as disclosed herein, systems and methods are provided that leverage computers, and specifically a network like the Internet, to provide understandable information to a patient and to obtain meaningful consent from the patient (e.g., consent is obtained from a patient once it is clear that the patient fully understands the content of the information that was provided). In particular, the systems and methods described herein may integrate with an electronic medical records (EMR) system to provide information to a patient. Such information may include an explanation of a how a procedure or treatment may be performed, possible complications or side effects that may occur, what a patient should do pre-op, what a patient should do during the procedure or treatment, and/or what a patient should do or expect post-op.

The information can be presented in a video format, where one or more videos can be presented to the patient and the videos can be constructed based on the diagnosis of the patient and/or other criteria (e.g., age of the patient, past medical history, etc.). The content of the videos can include diagnostic videos (e.g., information about the problem or diagnosis), treatment videos (e.g., information about the procedure or treatment, the post-operative care, and/or possible complications), and/or consent videos (e.g., information included in diagnostic videos and/or treatment videos). The videos can be available for viewing on a device in the practitioner's office and/or on a device owned by the patient (e.g., a laptop, a cell phone, a tablet, etc.). During a video, the patient can be asked a series of questions based on the content of the video. Based on the answers provided by the patient, the system described herein can gauge the patient's level of understanding of the information provided and either provide more, less, or other information in a subsequent video. Thus, the videos can be presented to the patient in a non-linear fashion.

In addition, the systems and methods described herein can monitor the patient as the videos are being watched to ensure that the patient is paying attention. For example, a camera can be used to track the patient's eyes to make sure that the patient is paying attention to the video. Likewise, the patient can be prompted to enter a code, say a word, click a button, make a gesture, and/or the like to confirm that the patient is paying attention to the video. Such monitoring information can be used and analyzed to determine whether the patient can provide meaningful consent. Moreover, such monitoring information can be stored for use in future litigation and/or the like as evidence that the patient was or was not paying attention to the videos.

Once the patient has finished watching the videos, the patient can be prompted to provide consent for the procedure or treatment. Consent can be provided and validated using one of several techniques, including an electronic or handwritten signature, a face imprint (e.g., a picture taken of the patient's face as a confirmation that consent is provided), the detection of facial movements (e.g., a camera can watch the patient's face, where a nod indicates consent is provided and a shake indicates consent is not provided), a voice imprint (e.g., a recording of the patient's voice to confirm that consent is provided), a fingerprint scan, a combination of the detection of facial movements and the voice imprint, the completion of the watching of one or more videos, the answering of one or more questions embedded in one or more videos, standard authentication protocols (e.g., a login and password), and/or the like. The obtained consent can then be provided to the practitioner for his or her records.

In this way, an interactive video can be used to provide understandable information to a patient and to confirm that the patient understands the information provided, and the functionality of a readily available computing device (e.g., a cell phone) can be used to monitor the patient and to obtain consent from the patient. Unlike traditional ways of obtaining consent, in which only the patient's signature is available to show that consent was provided, the system described herein leverages computing devices to provide an additional benefit in being able to track whether the patient paid attention to the information being provided and the manner by which consent was obtained. Such information can be stored and provided when necessary. For example, the information can be provided during litigation to prove or disprove that the patient understood the information provided by the practitioner and gave meaningful consent. Thus, the availability of such evidence could lower the likelihood of frivolous lawsuits. In fact, insurance companies may be willing to lower premiums for practitioners that use the systems and methods described herein because of such benefits (e.g., a percentage or nominal discount each time the systems and methods described herein are used by a patient, a percentage or nominal discount each time a video is watched by a patient, a flat discount if the practitioner uses the systems and methods described herein, etc.). Because one or more videos can be used to provide information and obtain consent, the system described herein can be referred to as the "Vonsent" (e.g., the word "video" combined with the word "consent") system. FIGS. 1-11 describe the Vonsent system in more detail below.

FIG. 1 is a block diagram depicting an exemplary communications system 100. The communications system 100 can include several devices, systems, and/or servers. For example, the communication system 100 can include an electronic medical records (EMR) system 110, a healthcare provider device 130, a Vonsent server 140, one or more user devices 150, one or more medical devices 160, and/or a network 120. The EMR system 110, the healthcare provider device 130, the one or more medical devices 160, the one or more user devices 150, and/or the Vonsent server 140 can all communicate via the network 120.

The EMR system 110 can be a system that monitors the medical history or medical data of a patient. The EMR system 110 can be accessed by the practitioner and the EMR system 110 can be located at the practitioner's office or can be located remotely (e.g., in which case the practitioner can access the EMR system 110 via a remote portal, such as a web portal). In an embodiment, the EMR system 110 includes an interface, such as a graphical user interface, by which a practitioner can view information about a patient, upcoming appointments, lab results, and/or the like. In addition, the interface can include a link to request or access data provided by the Vonsent server 140, which is described in greater detail below. For example, the link can allow a practitioner to request that a video related to a procedure or treatment be sent to a patient. As another example, the link can allow a practitioner to view consent data (e.g., whether a patient has provided consent for a certain procedure or treatment), monitoring information (e.g., data captured when tracking whether the patient is paying attention to a video), and/or other related medical information.

The healthcare provider device 130 can be located at the practitioner's office. The healthcare provider device 130 can be a portal that provides access to one or more EMR systems, such as the EMR system 110. For example, the healthcare provider device 130 can be a computer, tablet, or the like. The healthcare provider device 130 can also be configured to communicate directly or indirectly with the one or more medical devices 160, which are described in greater detail below.

The Vonsent server 140 can be a computing system that provides information to patients (e.g., via generated videos) and facilitates the obtaining of consent from patients. For example, the Vonsent server 140 can provide patients with access to diagnostic videos, treatment videos, and/or consent videos. As another example, the Vonsent server 140 can store information related to the monitoring of patients as they watch the videos to ensure that the patients are paying attention to the videos. As another example, the Vonsent server 140 can store information related to the manner by which consent was provided and/or an indication that consent was provided by the patient to a procedure or treatment.

The Vonsent server 140 can also be configured to provide notifications to a patient to inform them that an appointment has been scheduled, to remind patients about steps they should take after the procedure or treatment is complete (e.g., take certain medication, exercise, only eat certain food, etc.), to remind the patient of upcoming appointments, and/or to ask follow-up questions once a procedure or treatment has been completed (e.g., perform a virtual examination, asking the patient whether he or she had any pain and when, asking the patient what happened post-op, asking the patient if he or she had any trauma, etc.). Such notifications can be transmitted to a device owned or operated by the patient (e.g., the healthcare provider device 130, the one or more user devices 150, etc.). For example, the Vonsent server 140 can schedule appointments for a patient or remind patients about steps they should take based on the diagnosis, the patient's medical history, the type of procedure or treatment, complications that occurred after the procedure or treatment, and/or how well the patient understood the content of the diagnostic, treatment, and/or consent videos (e.g., if the patient watched the videos several times and/or answered questions incorrectly so that additional videos were provided to the patient for viewing, then the patient may not understand the content as well and additional reminders can be provided and/or appointments can be scheduled).

As another example, the Vonsent server 140 can store a list of appointments for one or more patients and provide reminders to a device operated by the patient regarding a particular appointment. As another example, the Vonsent server 140 can perform a virtual examination by asking patients follow-up questions (e.g., pain management questions, questions asked by practitioners when examining a patient. etc.) based on the patient's diagnosis, procedure, treatment, medical history, etc. The Vonsent server 140 can be configured to schedule further appointments for that patient with a practitioner and/or provide additional medical information (e.g., based on answers provided by the patient to the follow-up questions, based on how many questions a patient answered correctly or incorrectly while watching the initial diagnostic, treatment, and/or consent videos, etc.). Note that any information received from the patient (e.g., from the virtual examination) can be forwarded to the EMR system 110 and/or the healthcare provider device 130 for storage and/or for providing the practitioner with additional information The one or more user devices 150 can be any electronic device associated with a user, such as a patient. For example, the user device 150 can be a cell phone, laptop, tablet, desktop computer, and/or the like. The one or more user devices 150 can be configured to access content (e.g., videos) that is provided by the Vonsent server 140 via the network 120 and present such content to the patient. For example, the Vonsent server 140 can include a user account associated with a patient. Using the one or more user devices 150, a patient can enter a login and password to access the patient's user account. The user account can be associated with one or more videos and/or other medical information tailored to the patient, and the patient can access this content and information once logged in. Note that the user account can be associated with the patient based on a unique identifier (e.g., a name, an email address, an IP address, a medium access control (MAC) address, etc.), an age of the patient, and/or contact information for the patient (e.g., a mailing address, a phone number, etc.). In this way, the Vonsent server 140 and the techniques described herein can be in compliance with any relevant privacy laws (e.g., the Health Insurance Portability and Accountability Act (HIPAA) privacy and security rules).

The one or more user devices 150 can also be configured to monitor the patient to ensure that the patient is paying attention to the content and to obtain consent from the patient. For example, the one or more user devices 150 can include hardware components that can be used to monitor the patients and/or to obtain consent, as described in greater detail below. The one or more user devices 150 can also be configured to communicate directly or indirectly with the one or more medical devices 160, which are described in greater detail below.

In some embodiments, a patient can also access content and/or information stored on the Vonsent server 140 using the healthcare provider device 130. For example, like with the one or more user devices 150, using the healthcare provider device 130, a patient can enter a login and password to access the patient's user account. The user account can be associated with one or more videos and/or other medical information tailored to the patient, and the patient can access this content and information once logged in.

The one or more medical devices 160 can be any electronic device that is configured to diagnose, monitor, prevent, and/or treat a medical condition. The one or more medical devices 160 can be configured to capture or acquire medical measurements or activity data and transmit such data to another device (e.g., the healthcare provider device 130 and/or the one or more user devices 150). For example, the one or more medical devices 160 could be a heart rate monitor, a pacemaker, an insulin pump, an operating room monitor, a pedometer, and/or the like. The one or more medical devices 160 can be external to a user and/or implanted within the user. For example, the medical measurements could include a patient's vital signs (e.g., the heart rate of a patient, the breathing rate of a patient, the blood-sugar level of the patient, etc.). The one or more medical devices 160 can be connected, either wired or wirelessly, with the one or more user devices 150 and/or the healthcare provider device 130. In this way, the one or more medical devices 160 can capture or obtain medical data and then transmit that data to the one or more user devices 150 and/or the healthcare provider device 130. The one or more user devices 150 and/or the healthcare provider device 130 can then transmit the medical data to the EMR system 110, via the network 120.

The EMR system 110, the healthcare provider device 130, and/or the one or more user devices 150 can be embodied as a computer system, such as, without limitation, a laptop, a desktop, a tablet, a smartphone, a cell phone, or the like.

In an embodiment, the Vonsent server 140 include or are in communication with one or more storage mediums. For example, the Vonsent server 140 can include or be in communication with one or more databases. Such databases are described in greater detail below with respect to FIG. 3.

The Vonsent server 140 can be a computing device. For example, the Vonsent server 140 can include one or more processors to execute one or more instructions, memory, and communication devices to transmit and receive data over the network 120. In some embodiments, the Vonsent server 140 is implemented as one or more backend servers capable of communicating over a network. In other embodiments, the Vonsent server 140 is implemented by one more virtual machines in a hosted computing environment. The hosted computing environment can include one or more rapidly provisioned and released computing resources, which computing resources can include computing, networking and/or storage devices. A hosted computing environment can also be referred to as a cloud computing environment. In still other embodiments, the Vonsent server 140 can be represented as a user computing device capable of communicating over a network, such as a laptop or tablet computer, personal computer, personal digital assistant (PDA), hybrid PDA/mobile phone, mobile phone, global positioning system (GPS) device, or the like. Although FIG. 1 depicts a single Vonsent server 140, the functions described herein can be performed or distributed across multiple networked computing devices, including devices that are geographically distributed and/or are allocated dynamically from a pool of cloud computing resources. For example, the Vonsent server 140 can be implemented by one more virtual machines in a hosted computing environment. The hosted computing environment can include one or more rapidly provisioned and released computing resources (e.g., dynamically-allocated computing resources), which computing resources can include computing, networking and/or storage devices.

The network 120 can be a wired network, a wireless network, or a combination of the two. For example, the network 120 can be a personal area network, a local area network (LAN), a wide area network (WAN), or combinations of the same. Protocols and components for communicating via any of the other aforementioned types of communication networks, such as the TCP/IP protocols, can be used in the network 120.

In an embodiment, the devices and/or servers of the communications network 100 can be in communication with network 120 via wired or wireless technology. For example, devices and/or servers of the communications network 100 can communicate with network 120 via Ethernet, USB 1.0, USB 2.0, USB 3.0, IEEE 1394, IEEE 1394a, IEEE 1394b, Thunderbolt, VGA, DVI, HDMI, optical fiber, serial port, parallel port, the 802.11 standard, the 802.15.4 standard, radio-frequency identification (RFID), near-field communication (NFC), Bluetooth, or the like.

The messages and other communications transmitted between the various devices and servers in the communications system 100 as illustrated in FIG. 1 are described in more detail below with respect to FIG. 2.

Figure 2:
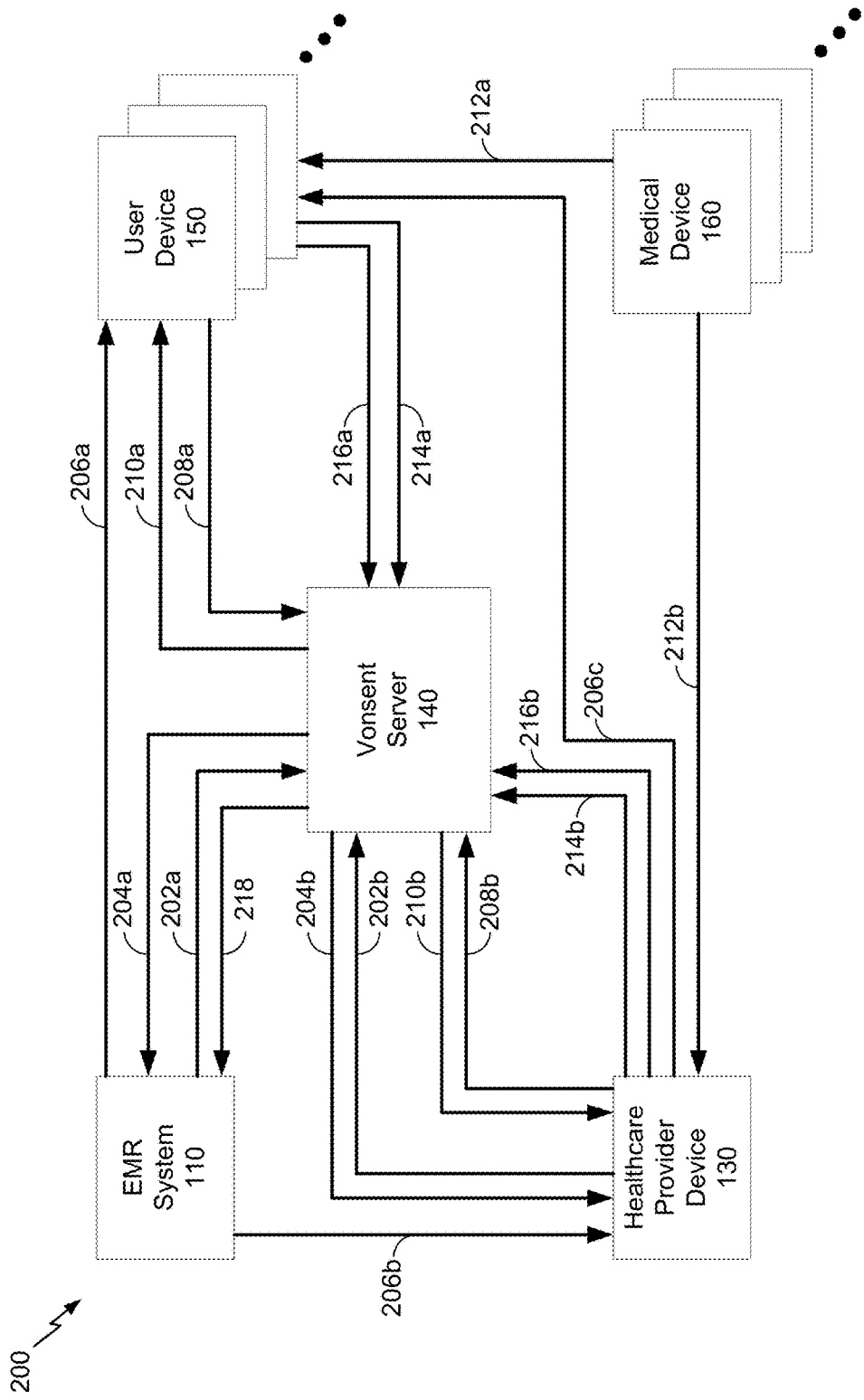
FIG. 2 is a block diagram depicting communications between the various devices and servers of the communications system of FIG. 1.

FIG. 2 is a block diagram depicting communications between the various devices and the servers of the communication system 100 of FIG. 1. As illustrated in FIG. 2, the EMR system 110 can transmit a message 202a to the Vonsent server 140. In an embodiment, once a practitioner has examined a patient and entered information related to the examination into an EMR system, such as the EMR system 110, the EMR system 110 can request certain information from the Vonsent server 140. For example, the practitioner can input a one or more diagnoses (e.g., medical codes, such as the International Classification of Diseases (ICD) medical codes) into the EMR system 110. The EMR system 110 can then transmit message 202a to the Vonsent server 140, which includes a request for a link to a video to be sent to the patient. In addition or alternatively, the message 202a to the Vonsent server 140 can include a request that a video be associated with the patient's user account so that the patient can view the video when logging into the user account.

After receiving the message 202a, the Vonsent server 140 can generate a link based on the one or more diagnoses. For example, the link can be to a video associated with the one or more diagnoses (e.g., a video that includes content related to a disease or condition identified by one or more medical codes). The link that is generated by the Vonsent server 140 can be transmitted to the EMR system 110 via message 204a.

In an alternate embodiment, the practitioner can use the healthcare provider device 130 rather than the EMR system 110. In that case, the healthcare provider device 130 can generate a message 202b, which includes the same content as message 202a, and transmit the message 202b to the Vonsent server 140. The Vonsent server 140 can generate a link based on the message 202b and forward that link to the healthcare provider device 130 via message 204b.

In an embodiment, the EMR system 110, after receiving the message 204a, can transmit the link to the one or more user devices 150 (e.g., the user device 150 associated with the patient that was diagnosed) so that the patient can view the content of the link. The link can be transmitted to the one or more user devices 150 via message 206a. In addition or alternatively, the EMR system 110 can transmit the link to the healthcare provider device 130 via message 206b. For example, the patient can be located in the practitioner's office and can use the healthcare provider device 130 located in the practitioner's office to provide the consent.

In an alternate embodiment, if the healthcare provider device 130 is the device that requested the link from the Vonsent server 140, then the healthcare provider device 130 can transmit the link to the one or more user devices 150 via message 206c.

Once the one or more user devices 150 receive the link either via message 206a or via message 206c, the patient, via the one or more user devices 150, can select the link. By selecting the link, an application executing on the one or more user devices 150 (e.g., a browser) can be directed to a portal (e.g., a website) where one or more videos can be viewed (e.g., either a portal that presents the videos or a portal that allows the patient to log in and view his or her account and access the videos). These videos can be stored and/or obtained via the Vonsent server 140. When the link is selected, message 208a (e.g., originating from the one or more user devices 150) or message 208b (e.g., originating from the healthcare provider device 130) is transmitted to the Vonsent server 140. Based on the message 208a or the message 208b, the Vonsent server 140 can prepare one or more videos for the patient to watch. These videos can be transmitted to the one or more user devices 150 via message 210a (e.g., if the Vonsent server 140 received message 208a) or to the healthcare provider device 130 via message 210b (e.g., if the Vonsent server 140 received message 208b).

In an embodiment, once the patient has finished watching the videos using the one or more user devices 150 or the healthcare provider device 130, the device used by the patient (e.g., the one or more user devices 150 and/or the healthcare provider device 130) can request consent from the patient. The consent can be requested in one of several ways, which are described in greater detail below.

In an embodiment, once the patient provides the consent, the consent can be transmitted to the Vonsent server 140 via message 214a (e.g., if the patient provided consent using the one or more user devices 150) or message 214b (e.g., if the patient provided consent using the healthcare provider device 130). In some embodiments, not shown, an indication that consent has been received can be forwarded to the EMR system 110.

The one or more medical devices 160 can transmit medical data to the one or more user devices 150 via message 212a and/or to the healthcare provider device 130 via message 212b. Once the one or more user devices 150 and/or the healthcare provider device 130 receive the medical data, the medical data can be forwarded to the Vonsent server 140 via message 216a (e.g., if the one or more user devices 150 receives the medical data) or message 216b (e.g., if the healthcare provider device 130 receives the medical data). In an embodiment, upon receiving the medical data, the Vonsent server 140 can forward the medical data to the EMR system 110 via message 218. The EMR system 110 can then associate the medical data with the appropriate patient and store such data.

Figure 3:
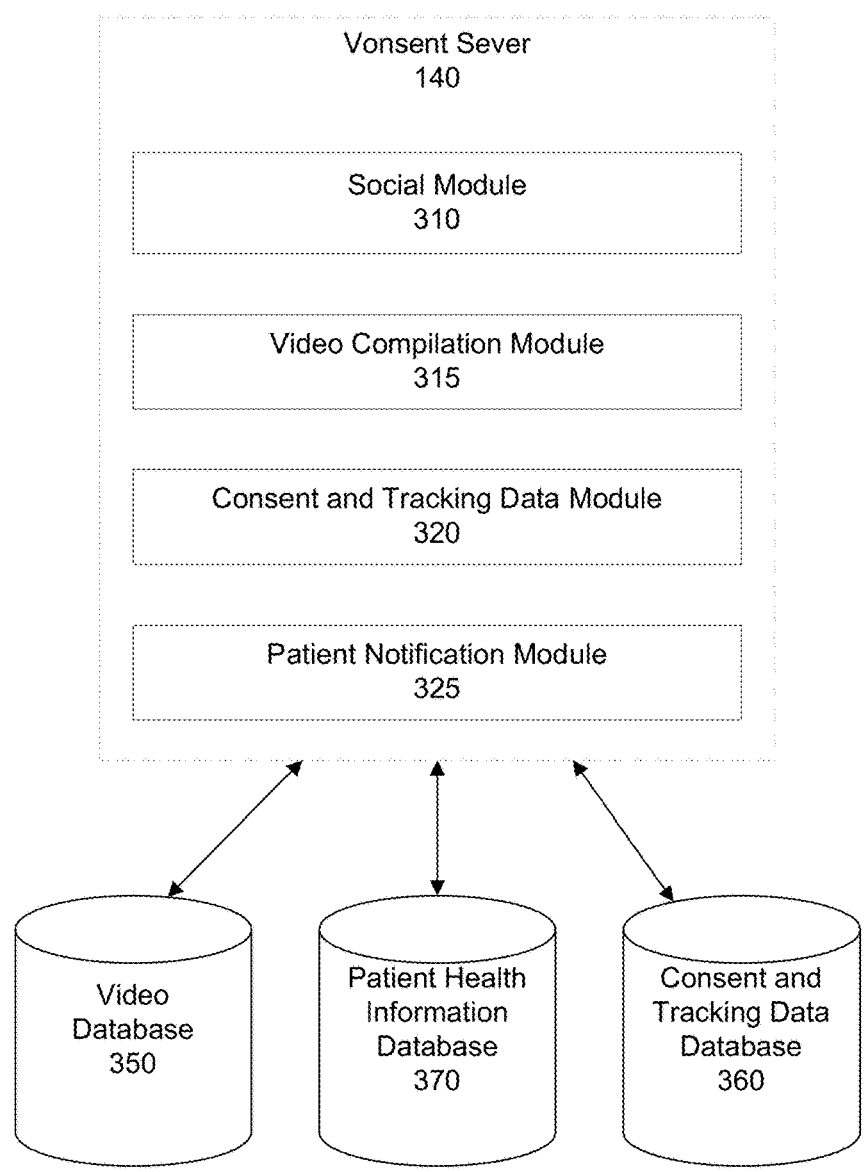
FIG. 3 is a more detailed block diagram of a server of the communications system of FIG. 1.

FIG. 3 is a more detailed block diagram of a server of the communications system 100 of FIG. 1. In particular, FIG. 3 is a more detailed block diagram of the Vonsent server 140. The Vonsent server 140 can include several modules. For example, the Vonsent server 140 can include a social module 310, a video compilation module 315, a consent and tracking data module 320, and a patient notification module 325.

The social module 310 can be configured to allow integration between a social media network (e.g., FACEBOOK, TWITTER, etc.) and the Vonsent server 140. For example, each patient can be associated with a user account as described above. By logging into the patient's specific user account using the one or more user devices 150 and/or the healthcare provider device 130, the patient can interact with other patients that have a similar diagnosis or are undergoing a similar procedure, with the functionality provided by the social module 310. Patients can contact these other patients to share recovery experiences and stories, information on surgical procedures, and/or the like via the user account.

The video compilation module 315 can be configured to generate a link based on a diagnosis that is received from the healthcare provider device 130 and/or the EMR system 110. For example, the link can be generated based on a medical code received from the healthcare provider device 130 and/or the EMR system 110. The link can direct a patient to a single set of videos if one medical code is received from the healthcare provider device 130 and/or the EMR system 110, the link can direct a patient to two sets of videos (that are presented in succession) if two medical codes are received from the healthcare provider device 130 and/or the EMR system 110 (e.g., where the first set of videos corresponds to the first medical code and the second set of videos corresponds to the second medical code), and so on. In addition or alternatively, the link can direct a patient to a first set of videos if two or more medical codes are received, where the first set of videos are more detailed than a second set of videos that would otherwise be presented to the patient if only a single medical code was received. The video compilation module 315 can also be configured to prepare and generate videos based on answers that are received from the one or more user devices 150 and/or the healthcare provider device 130, which is described in greater detail below. The video compilation module 315 can be further configured to store and retrieve videos that are stored in a video database 350.

The consent and tracking data module 320 can be configured to receive consent or an indication that consent has been provided by a patient from the one or more user devices 150 and/or the healthcare provider device 130. The consent and tracking data module 320 can store this information in consent and tracking data database 360. The consent and tracking data module 320 can also be configured to retrieve and store monitoring information from the one or more user devices 150 and/or the healthcare provider device 130, which is described in greater detail below. The monitoring information that is retrieved by the consent and tracking data module 320 can also be stored in the consent and tracking data database 360.

The patient notification module 325 can be configured to provide notifications and other information to patients. For example, the patient notification module 325 can notify patients of upcoming appointments with a practitioner, can remind patients of steps they should take or recommendations provided by the practitioner (e.g., take certain medication, exercise, not eat certain food, etc.), generate questions to ask of the patients after a procedure or treatment has been completed (e.g., perform a virtual examination), and/or schedule further appointments with the practitioner or provide more medical information to a patient based on a diagnosis, the procedure or treatment, complications that could occur or have occurred, the patient's medical history, answers received from the patient to questions presented after the procedure or treatment, and/or how many questions the patient answered correctly or incorrectly while watching the diagnostic, treatment, and/or consent videos. The medical information provided to patients by the patient notification module 325 can be retrieved from patient health information database 370. Note that any information received from the patient (e.g., from the virtual examination) can be forwarded to the EMR system 110 and/or the healthcare provider device 130 for storage and/or for providing the practitioner with additional information.

In an embodiment, the video database 350 is configured to store media (e.g., videos) used to provide information to patients about the problem or diagnosis, the procedure or treatment, the post-operative care, and/or possible complications. Questions and answers associated with the content of the stored media can also be stored in the video database 350.

In an embodiment, the consent and tracking data database 360 is configured to store the consent and/or an indication that consent has been provided by a patient. The consent and/or the indication that consent has been provided can be stored in an entry associated with the appropriate patient. The consent and tracking data database 360 can also be configured to store monitoring information received from the one or more user devices 150 and/or the healthcare provider device 130. The monitoring information can also be stored in an entry associated with the appropriate patient.

In an embodiment, the patient health information database 370 is configured to store medical information that can be provided to patients. For example, the medical information can be in the form of text, audio, video, and/or the like. The medical information can be associated in the patient health information database 370 with diagnoses, questions, answers, patients, etc.

In some embodiments, one or more of the databases described above can be implemented using a relational database, such as DB2, Sybase, MySQL, Oracle, CodeBase, and Microsoft® SQL Server as well as other types of databases such as a flat-file database, an entity relationship database, and object-oriented database, and/or a record-based database. The databases described above can be stored in a central repository or in different locations. The databases can be housed in a server apparatus or in a personal device, like a cell phone, a smart phone, a PDA, a tablet, a laptop, a desktop, a camera, a flash drive, a memory card, an optical disc, or the like. Note that while FIG. 3 depicts three databases, other embodiments can include more or fewer databases depending on the type of data a user can request. As is described herein, the Vonsent server 140 can run operating system software and a user can request data through a web-enabled user access point. Accordingly, a user can request any data available through the network 120 and supported by the operating system software.

Figure 4:
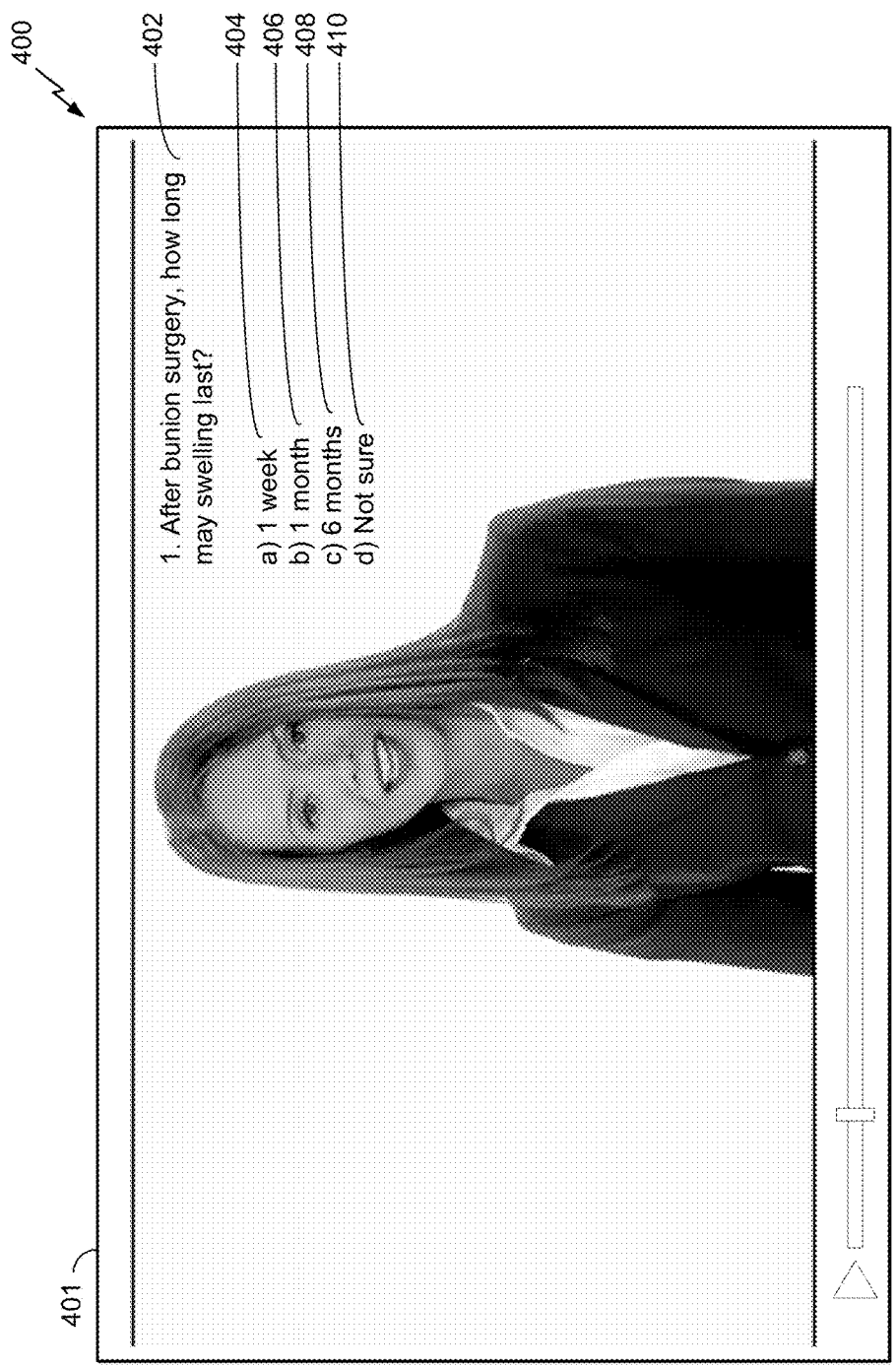
FIG. 4 is a diagram depicting an exemplary graphical user interface displaying an application executed by the healthcare provider device and/or the one or more user devices of the communications system of FIG. 1.

FIG. 4 is a diagram depicting an exemplary graphical user interface (GUI) 400 displaying an application executed by the healthcare provider device 130 and/or the one or more user devices 150 of the communications system 100 of FIG. 1. As illustrated in FIG. 4, the GUI 400 includes a video 401, which can be a diagnostic video, a treatment video, and/or a consent video.

As described above, several videos can be presented to the patient in a non-linear fashion. The videos may be received by the healthcare provider device 130 and/or the one or more user devices 150 from the Vonsent server 140 (e.g., via the video database 350). A second video, not shown, can be chosen based on a diagnosis associated with the user and/or an answer provided by the patient to a displayed question. For example, there can be one or more questions that are asked of the user based on the content of the video 401. The video 401 can be played and periodically paused or stopped so that a question can be asked of the patient. Depending on the answer provided by the patient, the video 401 can continue, a new video can be presented to the patient, and/or all of the videos can be completed.

As illustrated in FIG. 4, a question 402 is presented to the patient. Question 402 asks the patient: "After bunion surgery, how long may swelling last?" Several answers or potential answers are provided to the patient. For example, answer 404 provides an answer of "one week," answer 406 provides an answer of "one month," answer 408 provides an answer of "six months," and answer 410 provides an answer of "not sure." The patient can select one or more of the answers (e.g., by hovering over an answer, clicking on an answer, typing an answer, speaking an answer, etc.) and this information then can be transmitted to the Vonsent server 140. Once the Vonsent server 140 receives this information, the Vonsent server 140 can determine whether the video 401 should continue, whether another video should be presented to the user, and/or whether the video 401 should be completed.

Note that while question 402 is presented within the same windows as video 401, this is merely illustrative and is not meant to be limiting. For example, not shown, question 402 could be presented in a separate window, such as a pop-up window, a window adjacent to the video 401, a window overlapping the video 401, and/or the like. Likewise, question 402 could be presented to the patient using a device other than the device used to present the video 401, such as another user device 150 and/or the healthcare provider device 130. As another alternative, the question 402 could be verbally presented to the patient and the answer could be entered manually.

Figure 5:
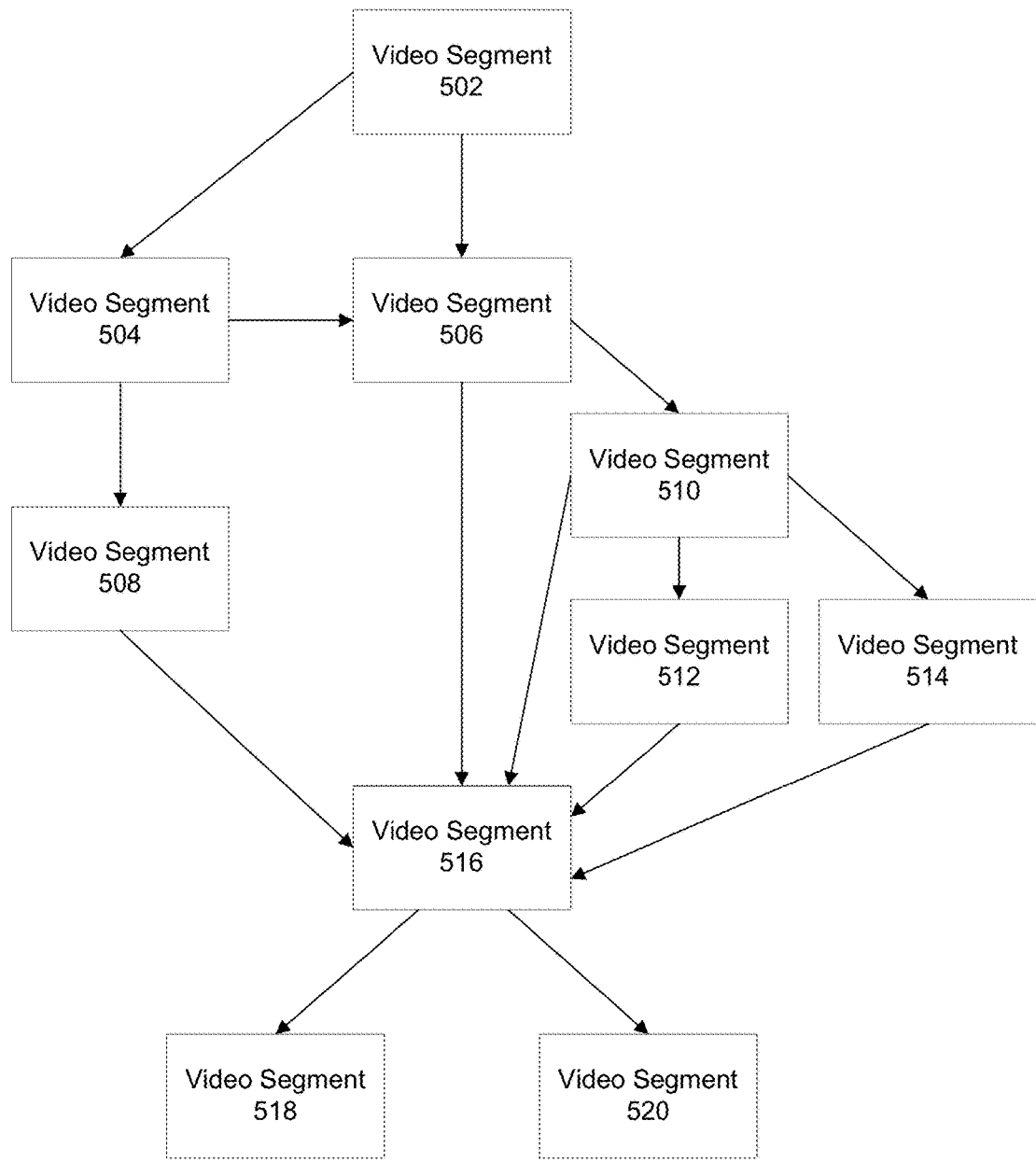
FIG. 5 is a diagram depicting an exemplary video tree that determines an order by which videos are presented to a user.

FIG. 5 is a diagram depicting an exemplary video tree that determines an order by which videos are presented to a user. As described above, one or more videos are presented to a patient via the one or more user devices 150 and/or the healthcare provider device 130. These videos can be generated and presented to the patient in a non-linear fashion. In other words, a series of videos can follow a set script. However, additional videos can be presented in between the series of videos that take exits from the script (e.g., to provide more information). For example, the videos can be generated and presented to the patient dynamically based on answers that are provided by the patient to questions presented during a video.

As illustrated in FIG. 5, a first video segment 502 can be presented to the patient. The first video segment 502 may include content that covers a single topic or subject. Once the patient has finished viewing at least a portion of the video segment 502, a question can be displayed in a manner as described above (e.g., the content of the question may be based on the single topic or subject). Based on the answer provided by the patient, video segment 502 can continue, video segment 502 can stop playback, and/or another video can be presented to the patient. For example, video segment 504 can be displayed if the patient provides a first answer. However, if a patient provides a second answer, then video segment 506 can be displayed. Likewise, if a patient provides a third answer, no more video segments can be displayed.

The differences in the video segments 504 and 506 can be related to what information the Vonsent server 140 determines should be provided to the patient based on the answer. If the patient provides the correct answer, then the storyline can continue and further information can be provided to the patient about other topics or subjects. However, if the patient incorrectly answers the question, then it can appear that the patient does not quite understand what was being presented in video segment 502. Video segment 502 could be shown again or another video segment can be displayed that provides more information on the topic or subject that was already presented in video segment 502. For example, if the patient incorrectly answers a question presented during video segment 502, then the patient can view video segment 504. Video segment 504 can include the same content as video segment 502, but video segment 504 can provide more detail on the content of video segment 502 (e.g., additional content related to the topic or subject of video segment 502).

As illustrated in FIG. 5, the above-described process continues for each additional video segment. For example, during video segment 504 another question can be presented to the patient. Based on the answer provided by the patient, video segment 506 or video segment 508 can be presented to the user. As described above, video segment 506 can include further information about other topics and can be presented to the patient if the patient selects the correct answer. However, video segment 508 can include more detailed information about the same topic as was presented in video segment 504 and/or the same topic presented in video segment 506 and can be presented to the patient if the patient selects an incorrect answer.

Another question can be presented to the patient during video segment 506 or video segment 508, and the patient can view one or more other video segments based on the answer. For example, video segment 510 can be presented to the patient if the patient answers incorrectly and video segment 516 can be presented to the patient if the patient answers correctly. During video segment 510 another question can be presented to the patient. In an embodiment, if the patient answers the question correctly, the patient is presented with video segment 516. If the patient answers with a first incorrect answer, then the patient is presented with video segment 512. Finally, if the patient answers with a second incorrect answer, then the patient is presented with video segment 514. As an example, the first incorrect answer can be closer to the correct answer than the second incorrect answer. Thus, video segment 514 can include more detailed information than video segment 512 on the same topic (e.g., where both video segments 512 and 514 include more detailed information on the same topic as presented in video segment 510).

In some embodiments, a question may or may not be presented during video segments 512 and/or 514. For example, more detailed information may not be available for presenting to the patient. In other embodiments, one or more questions may be presented during video segments 512 and/or 514. If the questions are answered correctly, the next video segment presented to the patient can be video segment 516. If the answers are not answered correctly, the same video segment (e.g., 512 or 514) can be repeated.

In an embodiment, during video segment 516, a question can be presented to the patient. Based on the answer provided by the patient, the patient can view video segment 518 or video segment 520. For example, video segment 520 can include more detailed information about the same topic as video segment 518 (e.g., video segment 520 is presented if the wrong answer is chosen and video segment 518 is presented if the correct answer is chosen).

In some embodiments, video segment 502 can be selected by the Vonsent server 140 based on the patient's diagnosis. Subsequent video segments can also be selected based on the patient's diagnosis. In other embodiments, video segment 502 can be the same for each patient regardless of the diagnosis. However, subsequent video segments can be selected based on the patient's diagnosis. For example, video segment 502 can be shown whether the patient's diagnosis is diabetes or heart disease. The patient can receive the same question during video segment 502 regardless of the diagnosis, but the next video segment presented to the patient can differ based on the diagnosis, even if the same answer is selected by the patient. In other words, if the patient selects answer "A" and the diagnosis is diabetes, the Vonsent server 140 determines that video segment 504 is the next video segment that should be presented to the patient. However, if the patient selects answer "A" and the diagnosis is heart disease, the Vonsent server 140 determines that video segment 506 is the next video segment that should be presented to the patient.

Note that if the video segments were instead presented in a linear order, then one path would exist from video segment 502 to video segment 516 (e.g., there would be no deviation from a script). The video segments are instead presented in a non-linear order because multiple paths exist from video segment 502 to video segment 516 (e.g., multiple video segments can be accessed after video segment 502, which ultimately lead to video segment 516, any given video segment can be repeated, a video segment can be repeated after another video segment is presented, etc.).

Generating and presenting videos to the patient in this non-linear fashion may reduce the memory utilization on the user devices 150 and/or the healthcare provider device 130. For example, instead of receiving and storing all video segments 502, 504, 506, 508, 510, 512, and 514 or receiving and storing one video segment that includes all of the content of the video segments 502, 504, 506, 508, 510, 512, and 514, the user devices 150 or the healthcare provider device 130 may only receive and store those video segments that are needed to ensure that the patient is fully informed and can provide meaningful consent.

While FIG. 5 illustrates video segments 502, 504, 506, 508, 510, 512, 514, 516, 518, and 520, this is not meant to be limiting. As can be understood by one skilled in the art, any number of video segments can be used to fully inform a patient and the paths between video segments can be organized in any manner.

FIG. 6 is a diagram depicting an exemplary healthcare provider device 130 and/or the one or more user devices 150 in the communications system 100 of FIG. 1. As described above, the patient can be monitored by the healthcare provider device 130 and/or the one or more user devices 150 to ensure that the patient is watching the video rather than just letting the video play while performing other tasks. In this way, by monitoring the patient and then storing this monitoring information in the consent and tracking data database 360, the Vonsent server 140 and the EMR system 110 will have the information available to inform a practitioner or other interested party that the patient has watched the videos. Because the videos are constructed in a non-linear fashion based on the patient's diagnosis and/or the answers selected by the patient to questions posed during the videos, the Vonsent server 140 and the EMR system 110 will also have the information available to inform the practitioner or other interested party that the patient understands the content of the videos and any consent obtained is meaningful.

As illustrated in FIG. 6, the one or more user devices 150 and/or the healthcare provider device 130 can include several devices that can be used to monitor the patient and to ensure that the patient is paying attention to the videos. For example, the one or more user devices 150 and/or the healthcare provider device 130 can include a camera 604, a touchscreen display 606, a fingerprint scanner 608, and/or a microphone 610. In addition, these devices can be used to provide consent, as described below.

In an embodiment, the camera 604 is used to monitor the patient as the patient is watching the video. For example, the camera 604 can track the eyes of the patient to see if the patient is looking at the one or more user devices 150 and/or the healthcare provider device 130 or in another direction. If the patient strays from the video (e.g., if the patient's eyes look away from the video), then the video can pause, the video can request that the user pay attention to the video, and/or other actions can be performed to ensure that the patient then does pay attention to the video. As another example, the camera 604 can recognize gestures made by the patient. To ensure that the patient is paying attention to the video, the video can randomly or periodically request that the patient make a gesture (e.g., via the patient's finger), such as by drawing a geometric shape, making a swipe, drawing a sign, and/or the like in the air and/or on the touchscreen display 606. The camera 604 could detect the gesture by selecting a point on a part of the patient's body that is making the gesture as a baseline (e.g., the tip of the patient's finger). The movement of the baseline point could be observed to determine whether the correct gesture is being made by the patient.

Likewise, the touchscreen display 606 can be used to track the patient. For example, the touchscreen display 606 can periodically present questions to the patient. The questions can be the same questions as described above or can be questions unrelated to the content of the videos. By answering the questions, the one or more user devices 150 and/or the healthcare provider device 130 can infer that the patient is paying attention to the videos. Alternatively or in addition, the touchscreen display 606 can display other information requesting the patient to perform certain actions. For example, the touchscreen display 606 can request that the patient rotate the one or more user devices 150 and/or the healthcare provider device 130, click a button, enter a password, and/or the like. By performing the requested task, the one or more user devices 150 and/or the healthcare provider device 130 can infer that the patient is paying attention to the videos. If the user does not answer the questions (or answer the questions correctly) and/or does not perform the requested tasks within a certain amount of time, then the video can pause and/or the one or more user devices 150 and/or the healthcare provider device 130 can request that the patient pay attention to the video.

In an embodiment, the fingerprint scanner 608 is used to monitor the patient. For example, the touchscreen display 606 can display a prompt requesting the patient to scan his or her finger to ensure that the patient is watching the video.

Likewise, the microphone 610 can be used to monitor the user. For example, the touchscreen display 606 can display a prompt requesting the patient to say his or her name or any word to ensure that the patient is at the device and watching the video. The captured voice can be compared with a stored voice sample to ensure that that it is the patient that spoke when prompted.

Other monitoring information can be gathered by the one or more user devices 150 and/or the healthcare provider device 130 as well. For example, the time spent watching the videos can be recorded, the time spent not watching the videos can be recorded, the total amount of time it took the patient to finish watching the videos, the Internet protocol (IP) address of the patient's device can be stored.

In an embodiment, the Vonsent server 140 can be the device that determines which of the components (e.g., the camera 604, the touchscreen display 606, the fingerprint scanner 608, and/or the microphone 610) is used to monitor the patient. For example, the Vonsent server 140 can be connected to the healthcare provider device 130 and/or the one or more user devices 150 via the network 120. The Vonsent server 140 can provide instructions to the healthcare provider device 130 and/or the user device 150 requesting that the healthcare provider device 130 and/or the user device 150 provide information on the input/output devices available for use on the particular device. Based on the input/output device information provided to the Vonsent server 140, the Vonsent server 140 can transmit instructions to the healthcare provider device 130 and/or the one or more user devices 150 instructing the particular device to use one or more of the components to monitor the patient. Information obtained while monitoring the patient (e.g., the amount of the time that the patient spent watching the video, the amount of time that the patient spent not paying attention to the video, the total amount of time that it took the user to view the videos, and/or other information) can be provided to the Vonsent server 140 and stored by the Vonsent server 140 in a database, such as the consent and tracking data database 360, as described above.

In an embodiment, the same components (e.g., the camera 604, the touchscreen display 606, the fingerprint scanner 608, and/or the microphone 610) can be used when requesting consent from the patient. For example, once the videos are complete and consent is requested from the patient, the camera 604 can be used take a picture of the patient as evidence that the patient is providing consent. As another example, the camera 604 can be used to track or detect facial movements of the patient as evidence that the patient is providing consent. A nod of the head could indicate consent is provided and a shake of the head could indicate consent is not provided. The camera 604 could detect the nod or shake (or any other facial movement that indicates whether consent is provided) by selecting a point on the patient's face as a baseline (e.g., the tip of the patient's nose). If the baseline point moves horizontally, that could be interpreted as a shake, and if the baseline point moves vertically, that could be interpreted as a nod. As another example, the touchscreen display 606 can be used to allow the patient to write and/or sign (e.g., using a stylus, a finger, etc.) his or her name as evidence of the consent. As another example, the touchscreen display 606 and/or any additional input/output devices (e.g., a mouse, a keyboard, etc.) can be used by the patient to enter a login and password. As another example, the fingerprint scanner 608 can be used to obtain consent where the patient can be prompted to scan his or her finger as evidence of consent being provided. As another example, a voice imprint can be captured as evidence of consent using the microphone 610. The captured voice can be compared to a stored sample to ensure that it is the patient that is providing the consent. As another example, the camera 604 can be used to track or detect facial movements of the patient and the microphone 610 can be used to record the patient's voice, the combination of which can be used as evidence that the patient is providing consent. To provide consent, the patient could nod his or her head and say "yes" (or some similar word). Likewise, to not provide consent, the patient could shake his or her head and say "no" (or some similar word). As another example, the completion of the watching of one or more videos and/or the answering of one or more questions embedded in one or more videos can be considered consent. As another example, any of the above examples could be used in combination as evidence that the patient is providing consent. The actual consent (e.g., the picture, the signature, the fingerprint scan, the voice imprint, etc.) can be captured by the healthcare provider device 130 and/or the one or more user devices 150 and transmitted to the Vonsent server 140. Alternatively or in addition, an indication that consent was provided can be transmitted to the Vonsent server 140. The Vonsent server 140 can store the actual consent and/or an indication that consent was provided in a database, such as the consent and tracking data database 360.

In an embodiment, if consent is not obtained (e.g., the patient explicitly does not provide consent, the patient incorrectly answers questions indicating that the patient lacks understanding, etc.), one of several procedures can be employed by the Vonsent server 140. For example, the Vonsent server 140 can flag the patient as not having provided consent and transmit such information to the EMR system 110 and/or the healthcare provider device 130 to inform the practitioner that consent has not provided (e.g., so the practitioner can contact the patient to remedy the situation). As another example, the Vonsent server 140 can generate a recommendation as to whether the procedure or treatment should proceed and provide such recommendation to the practitioner via the EMR system 110 and/or the healthcare provider device 130. In some embodiments, the Vonsent server 140 could analyze the risk in performing the procedure or treatment in order to generate the recommendation based on patient data, such as age, gender, medical history, and/or the like, and/or based on a percentage of questions answered correctly (e.g., if the percentage of questions answered correctly is below a threshold, then the recommendation could be to not proceed with the procedure or treatment). As another example, the Vonsent server 140 could prevent the practitioner from accepting payment from the patient and/or prevent the patient from paying for the procedure or treatment. As another example, the Vonsent server 140 could establish a video link (e.g. a live video link) between the patient (e.g., via the one or more user devices 150) and the practitioner's office (e.g., via the EMR system 110 and/or the healthcare provider device 130). While communicating with the patient via the video link, the EMR system 110 and/or the healthcare provider device 130 can be configured to display the questions that the patient answered incorrectly. Such information can be provided to the EMR system 110 and/or the healthcare provider device 130 by the Vonsent server 140.

Figure 7A:
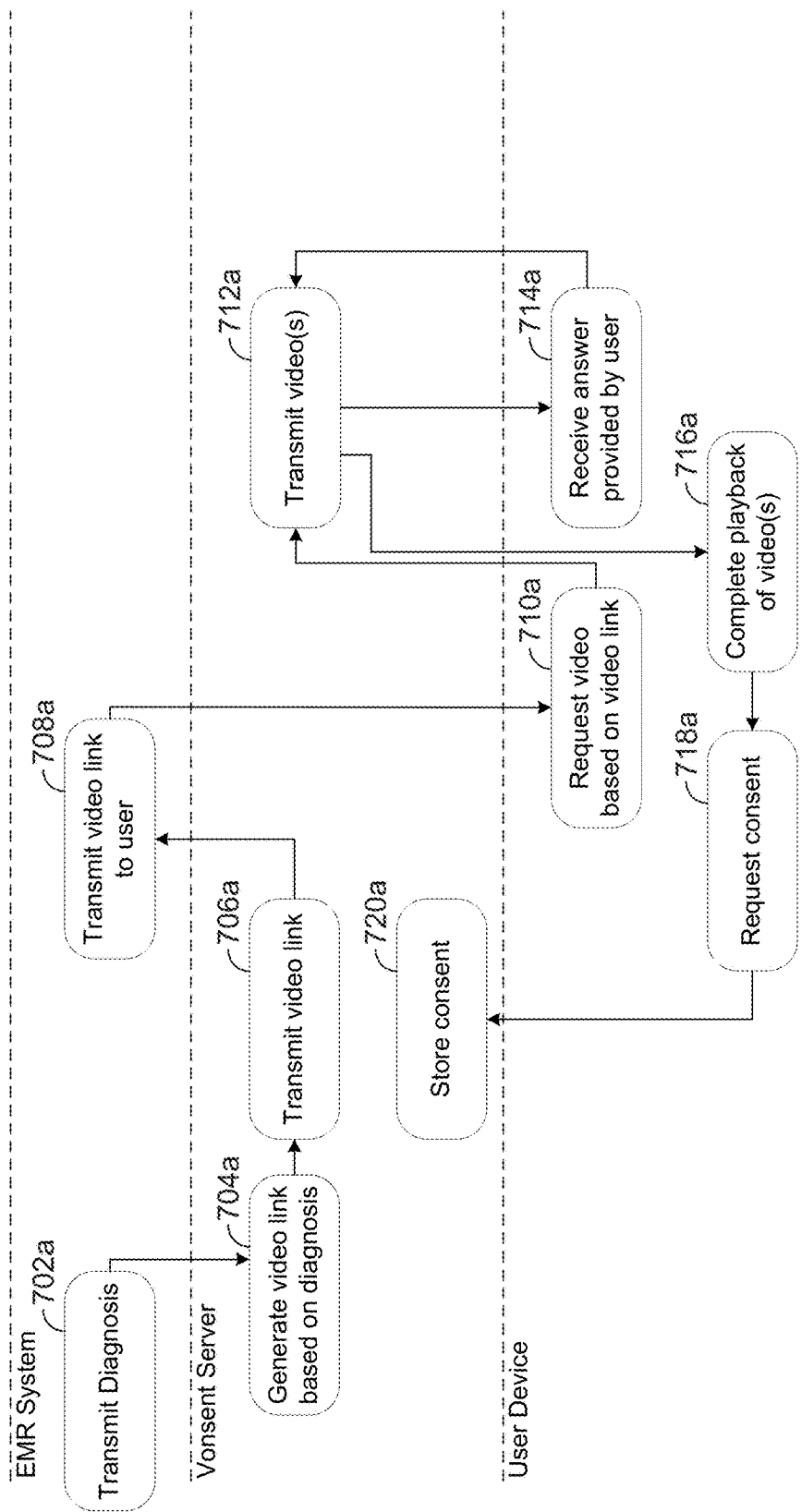
FIGS. 7A-C are flow diagrams depicting a process for obtaining consent from a patient.
Figure 7B:
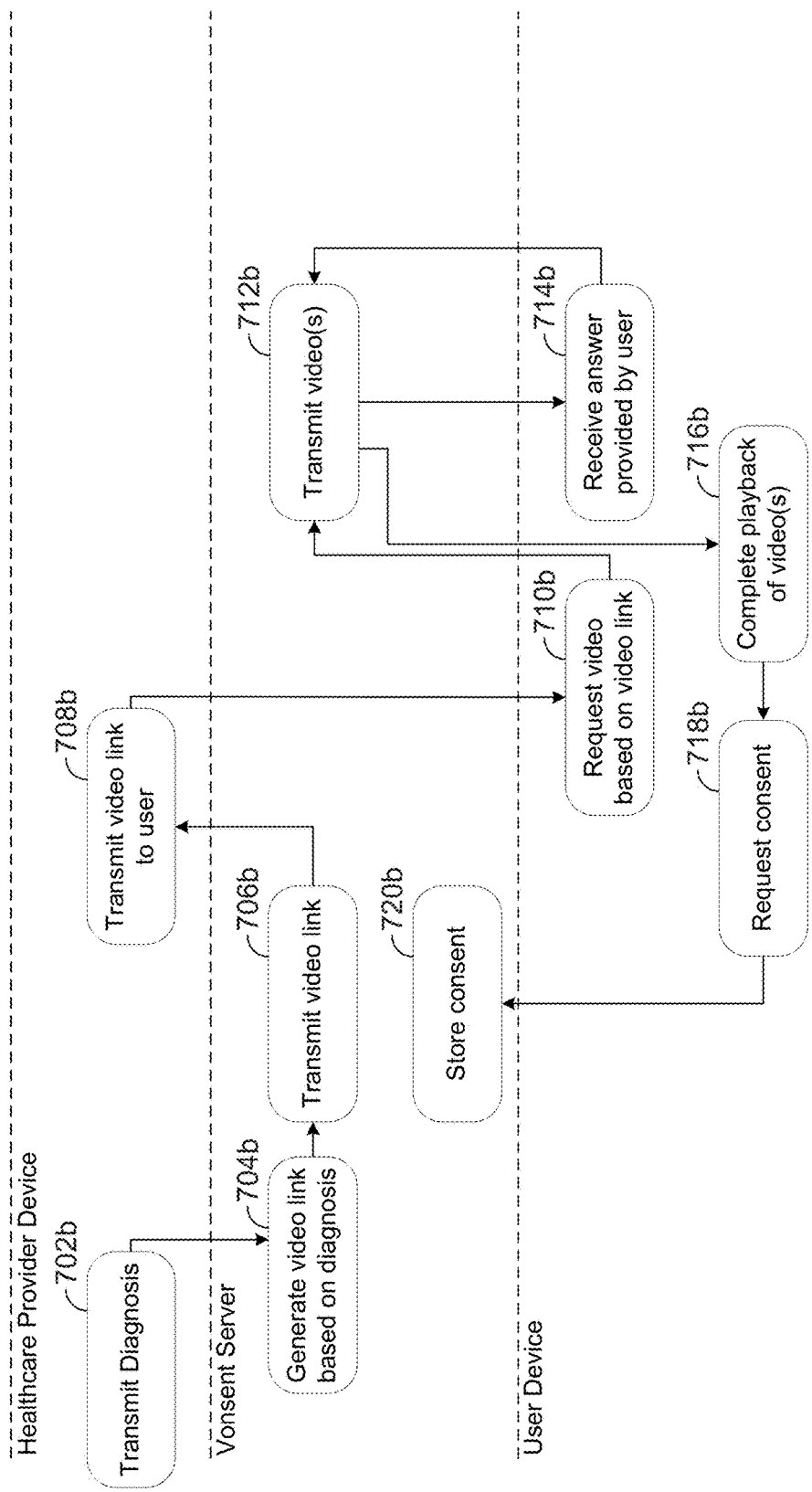
Figure 7C:
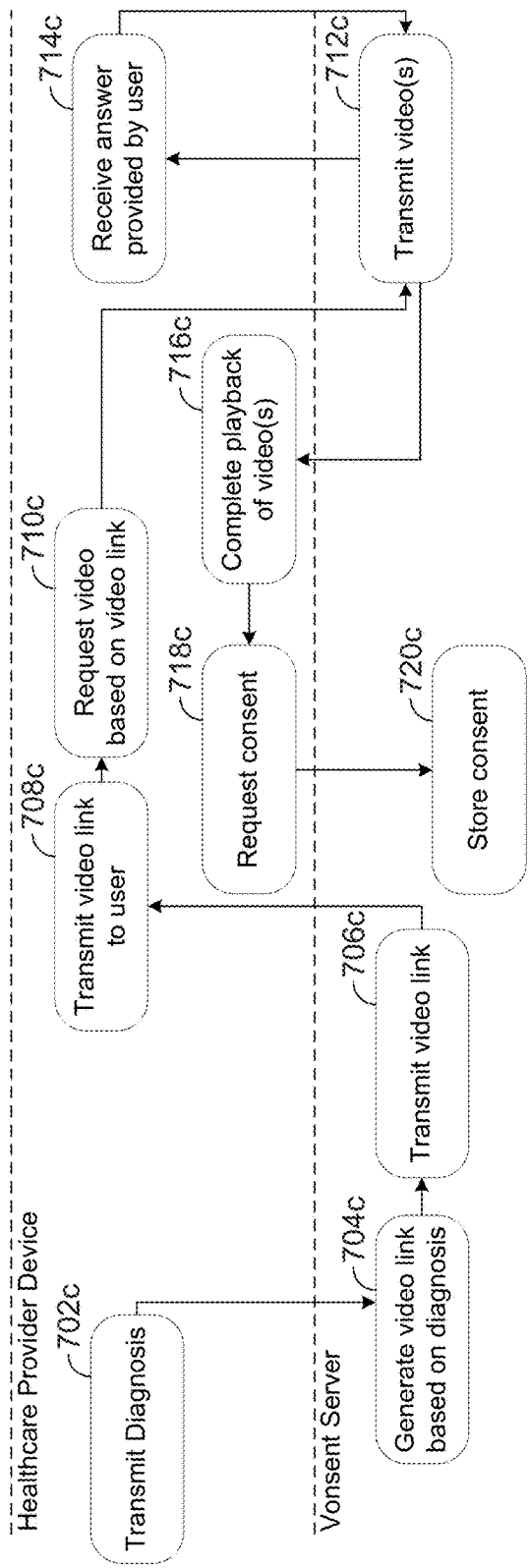

FIGS. 7A-7C are flow diagrams depicting a process for obtaining consent from a patient. In particular, FIG. 7A is a flow diagram depicting a process 700 for obtaining consent from a patient using the EMR system 110, the Vonsent server 140, and the user device 150. As illustrated in FIG. 7A, a diagnosis can be transmitted by an EMR system 110 to the Vonsent server 140 at box 702a. At box 704a, the Vonsent server 140 receives the diagnosis and generates a video link based on the diagnosis. At box 706a, the Vonsent server 140 then transmits the video link to the EMR system 110.

At box 708a, the EMR system 110 receives the video link and transmits the video link to the user via the user device 150. At box 710a, the user device 150 receives the video link and, based on the video link, the user device 150 can request the video. The video can be requested from the Vonsent server 140 when the user selects the link. At box 712a, the Vonsent server 140 receives the request for the video and transmits the video to the user device 150. At box 714a, the user device 150 receives the video. During playback of the video, a question based on the content of the video is presented to the user. At box 714a, the user provides an answer to the question and the user device 150 transmits the answer to the Vonsent server 140. Based on the answer received by the Vonsent server 140, the Vonsent server 140 may transmit another video 712a to the user device 150 or may not transfer any further videos. If the Vonsent server 140 does transmit another video, box 714a is repeated. If the Vonsent server 140 does not transmit another video, the playback of the video is completed by the user device 150 at block 716a. At box 718a, the user device 150 requests that the user provide consent for a procedure or treatment that will be performed. Upon obtaining this consent, the consent is transmitted to the Vonsent server 140. At box 720a, the Vonsent server 140 stores the consent.

FIG. 7B is a flow diagram depicting a process 730 for obtaining consent from a patient using the healthcare provider device 130, the Vonsent server 140, and the user device 150. As illustrated in FIG. 7B, a diagnosis can be transmitted by a healthcare provider device 130 to the Vonsent server 140 at box 702b. At box 704b, the Vonsent server 140 receives the diagnosis and generates a video link based on the diagnosis. At box 706b, the Vonsent server 140 then transmits the video link to the healthcare provider device 130.

At box 708b, the healthcare provider device 130 receives the video link and transmits the video link to the user via the user device 150. At box 710b, the user device 150 receives the video link and, based on the video link, the user device 150 can request the video. The video can be requested from the Vonsent server 140 when the user selects the link. At box 712b, the Vonsent server 140 receives the request for the video and transmits the video to the user device 150. At box 714b, the user device 150 receives the video. During playback of the video, a question based on the content of the video is presented to the user. At box 714b, the user provides an answer to the question and the user device 150 transmits the answer to the Vonsent server 140. Based on the answer received by the Vonsent server 140, the Vonsent server 140 may transmit another video 712b to the user device 150 or may not transfer any further videos. If the Vonsent server 140 does transmit another video, box 714b is repeated. If the Vonsent server 140 does not transmit another video, the playback of the video is completed by the user device 150 at block 716b. At box 718b, the user device 150 requests that the user provide consent for a procedure or treatment that will be performed. Upon obtaining this consent, the consent is transmitted to the Vonsent server 140. At box 720b, the Vonsent server 140 stores the consent.

FIG. 7C is a flow diagram depicting a process 740 for obtaining consent from a patient using the healthcare provider device 130 and the Vonsent server 140. As illustrated in FIG. 7C, a diagnosis can be transmitted by a healthcare provider device 130 to the Vonsent server 140 at box 702c. At box 704c, the Vonsent server 140 receives the diagnosis and generates a video link based on the diagnosis. At box 706c, the Vonsent server 140 then transmits the video link to the healthcare provider device 130.

At box 708c, the healthcare provider device 130 receives the video link and transmits the video link to the user via the healthcare provider device 130. At box 710c, the healthcare provider device 130, based on the video link, requests the video. The video can be requested from the Vonsent server 140 when the user selects the link. At box 712c, the Vonsent server 140 receives the request for the video and transmits the video to the healthcare provider device 130. At box 714c, the healthcare provider device 130 receives the video. During playback of the video, a question based on the content of the video is presented to the user. At box 714c, the user provides an answer to the question and the healthcare provider device 130 transmits the answer to the Vonsent server 140. Based on the answer received by the Vonsent server 140, the Vonsent server 140 may transmit another video 712c to the healthcare provider device 130 or may not transfer any further videos. If the Vonsent server 140 does transmit another video, box 714c is repeated. If the Vonsent server 140 does not transmit another video, the playback of the video is completed by the healthcare provider device 130 at block 716c. At box 718c, the healthcare provider device 130 requests that the user provide consent for a procedure or treatment that will be performed. Upon obtaining this consent, the consent is transmitted to the Vonsent server 140. At box 720c, the Vonsent server 140 stores the consent.

Figure 8A:
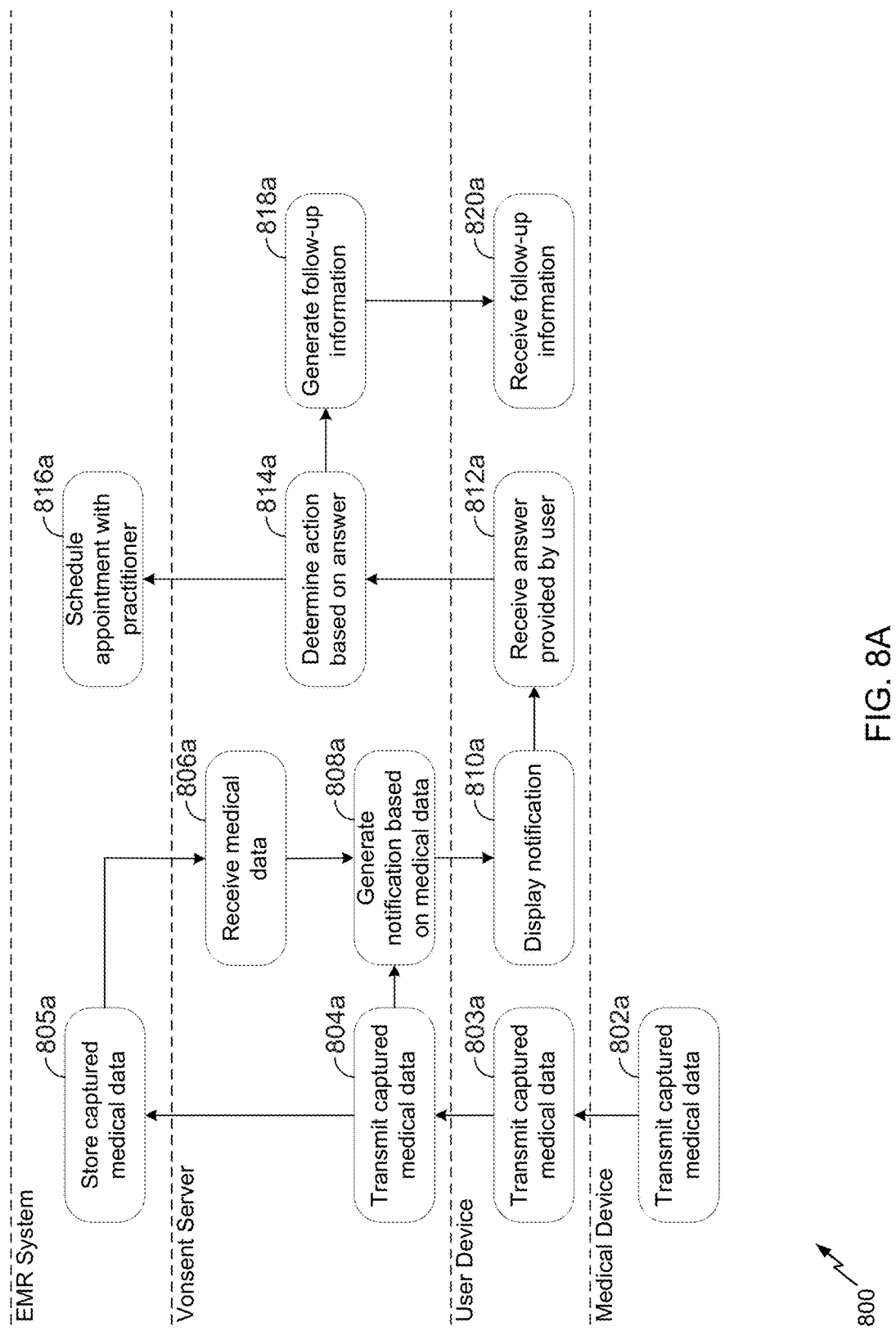
FIGS. 8A-C are flow diagrams depicting a process for performing a follow-up consultation with a patient.
Figure 8B:
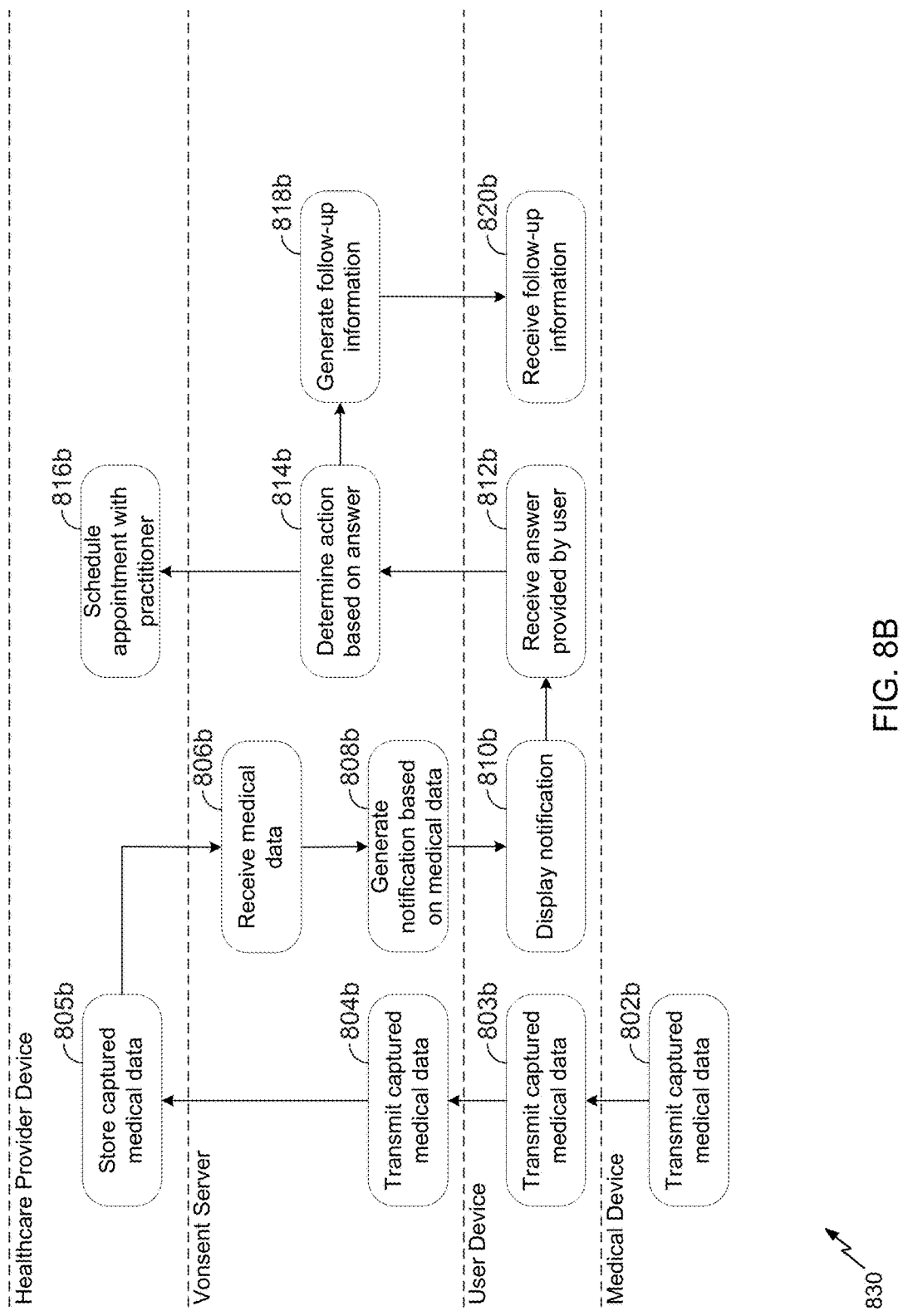
Figure 8C:
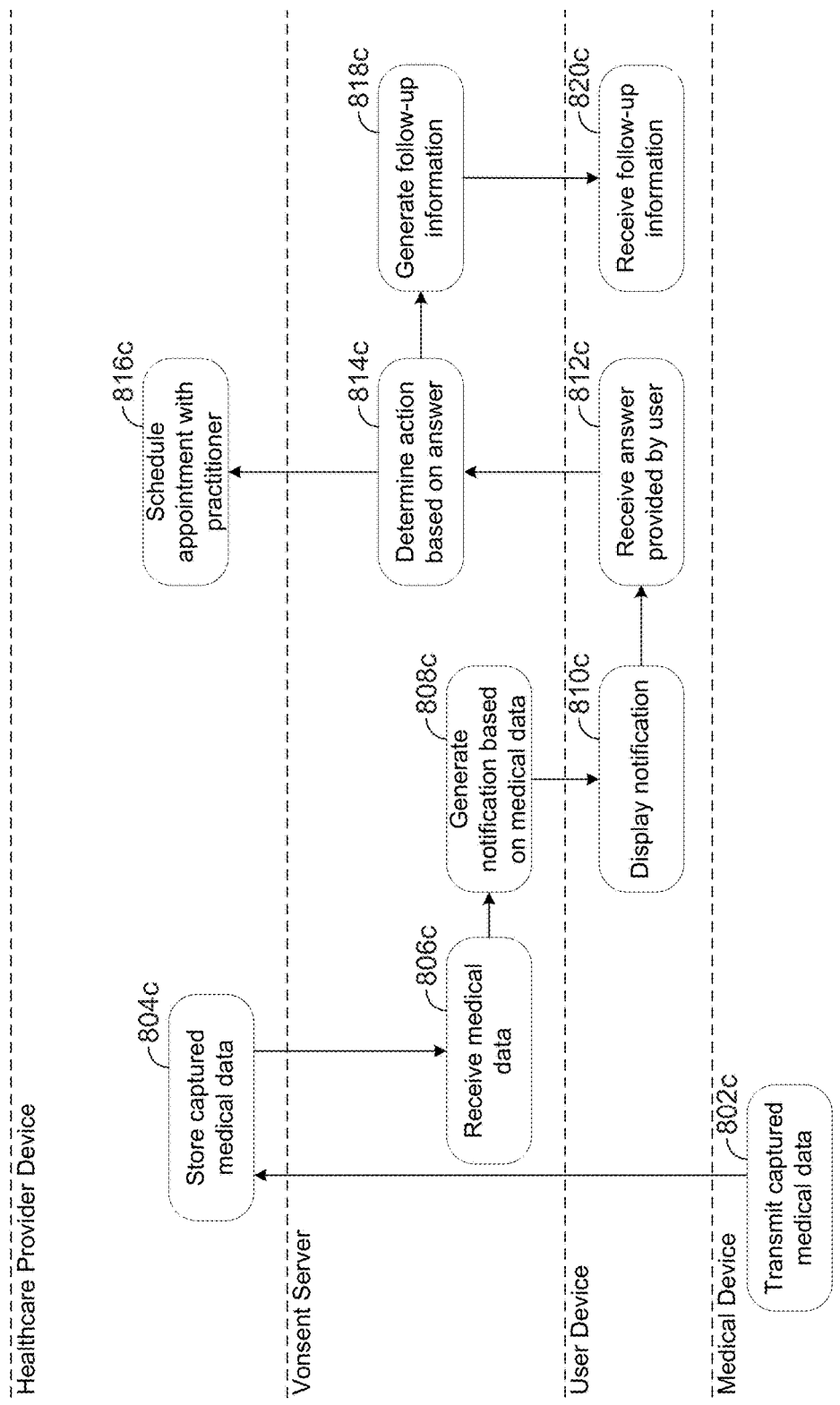

FIGS. 8A-8C are flow diagrams depicting a process for performing a follow-up consultation with a patient. In particular, FIG. 8A is a flow diagram depicting a process 800 for performing a follow-up consultation with a patient using the EMR system 110, the Vonsent server 140, the user device 150, and the medical device 160. At block 802a, the medical device 160 can first capture medical data and then transmit such medical data to the user device 150. At block 803a, the user device 150 can receive this transmitted medical data and forward the medical data to the Vonsent server 140. At block 804a, the Vonsent server 140 can receive the medical data and then transmit that medical data to the EMR system 110. Alternatively, at block 804a, the Vonsent server 140 can receive the medical data and store the medical data. At block 805a, the EMR system 110 can then store the captured medical data. At that time, or at a later time, the EMR system 110 can transmit stored medical data to the Vonsent server 140. The stored medical data can include the most recently captured medical data and/or medical data that was captured at a previous time.

At block 806a, the Vonsent server 140 can receive the medical data. At block 808a, the Vonsent server 140 can generate a notification based on the received medical data and/or any stored medical data. For example, the notification can be a reminder that an appointment with the practitioner is coming up soon. The notification can include a question to ask of the patient (e.g., the question can be a follow-up question to ask how the patient is doing after a procedure or medical treatment has been performed). This notification can then be transmitted to the user device 150.

At block 810a, the user device 150 can display the notification. If the notification includes a question of the patient, the user device 150, at block 812a, can receive an answer selected by the patient. This answer can then be transmitted to the Vonsent server 140. At block 814a, the Vonsent server 140 can determine an action to be performed based on the answer provided by the user device 150. For example, if the action can be that an appointment needs to be scheduled with a practitioner, the Vonsent server 140 can transmit an indication that an appointment needs to be scheduled to the EMR system 110. At block 816a, the EMR system 110 can then schedule an appointment with a practitioner. As another example, an action can be that follow-up information (e.g., follow-up medical information) needs to be provided to the patient. At block 818a, the Vonsent server 140 can then generate the follow-up information and transmit the follow-up information to the user device 150. At block 820a, the user device 150 receives the follow-up information and displays the follow-up information to the patient.

FIG. 8B is a flow diagram depicting a process 830 for performing a follow-up consultation with a patient using the healthcare provider device 130, the Vonsent server 140, the user device 150, and the medical device 160. At block 802b, the medical device 160 can first capture medical data and then transmit such medical data to the user device 150. At block 803b, the user device 150 can receive this transmitted medical data and forward the medical data to the Vonsent server 140. At block 804b, the Vonsent server 140 can receive the medical data and then transmit that medical data to the healthcare provider device 130. Alternatively, at block 804b, the Vonsent server 140 can receive the medical data and store the medical data. At block 805b, the healthcare provider device 130 can store the captured medical data or forward the captured medical data to an EMR system for storage. At that time, or at a later time, the healthcare provider 130 can transmit stored medical data to the Vonsent server 140. The stored medical data can include the most recently captured medical data and/or medical data that was captured at a previous time.

At block 806b, the Vonsent server 140 can receive the medical data. At block 808b, the Vonsent server 140 can generate a notification based on the received medical data and/or any stored medical data. For example, the notification can be a reminder that an appointment with the practitioner is coming up soon. The notification can include a question to ask of the patient (e.g., the question can be a follow-up question to ask how the patient is doing after a procedure or medical treatment has been performed). This notification can then be transmitted to the user device 150.

At block 810b, the user device 150 can display the notification. If the notification includes a question of the patient, the user device 150, at block 812b, can receive an answer selected by the patient. This answer can then be transmitted to the Vonsent server 140. At block 814b, the Vonsent server 140 can determine an action to be performed based on the answer provided by the user device 150. For example, if the action can be that an appointment needs to be scheduled with a practitioner, the Vonsent server 140 can transmit an indication that an appointment needs to be scheduled to the healthcare provider device 130. At block 816b, the healthcare provider device 130 can then schedule an appointment with a practitioner. As another example, an action can be that follow-up information (e.g., follow-up medical information) needs to be provided to the patient. At block 818b, the Vonsent server 140 can then generate the follow-up information and transmit the follow-up information to the user device 150. At block 820b, the user device 150 receives the follow-up information and displays the follow-up information to the patient.

FIG. 8C is a flow diagram depicting a process 840 for performing a follow-up consultation with a patient using the healthcare provider device 130, the Vonsent server 140, the user device 150, and the medical device 160. At block 802c, the medical device 160 can first capture medical data and then transmit such medical data to the healthcare provider device 130. At block 804c, the healthcare provider device 130 can store the captured medical data or forward the captured medical data to an EMR system for storage. At that time, or at a later time, the healthcare provider 130 can transmit stored medical data to the Vonsent server 140. The stored medical data can include the most recently captured medical data and/or medical data that was captured at a previous time.

At block 806c, the Vonsent server 140 can receive the medical data. At block 808c, the Vonsent server 140 can generate a notification based on the received medical data and/or any stored medical data. For example, the notification can be a reminder that an appointment with the practitioner is coming up soon. The notification can include a question to ask of the patient (e.g., the question can be a follow-up question to ask how the patient is doing after a procedure or medical treatment has been performed). This notification can then be transmitted to the user device 150.

At block 810c, the user device 150 can display the notification. If the notification includes a question of the patient, the user device 150, at block 812c, can receive an answer selected by the patient. This answer can then be transmitted to the Vonsent server 140. At block 814c, the Vonsent server 140 can determine an action to be performed based on the answer provided by the user device 150. For example, if the action can be that an appointment needs to be scheduled with a practitioner, the Vonsent server 140 can transmit an indication that an appointment needs to be scheduled to the healthcare provider device 130. At block 816c, the healthcare provider device 130 can then schedule an appointment with a practitioner. As another example, an action can be that follow-up information (e.g., follow-up medical information) needs to be provided to the patient. At block 818c, the Vonsent server 140 can then generate the follow-up information and transmit the follow-up information to the user device 150. At block 820c, the user device 150 receives the follow-up information and displays the follow-up information to the patient.

Figure 9:
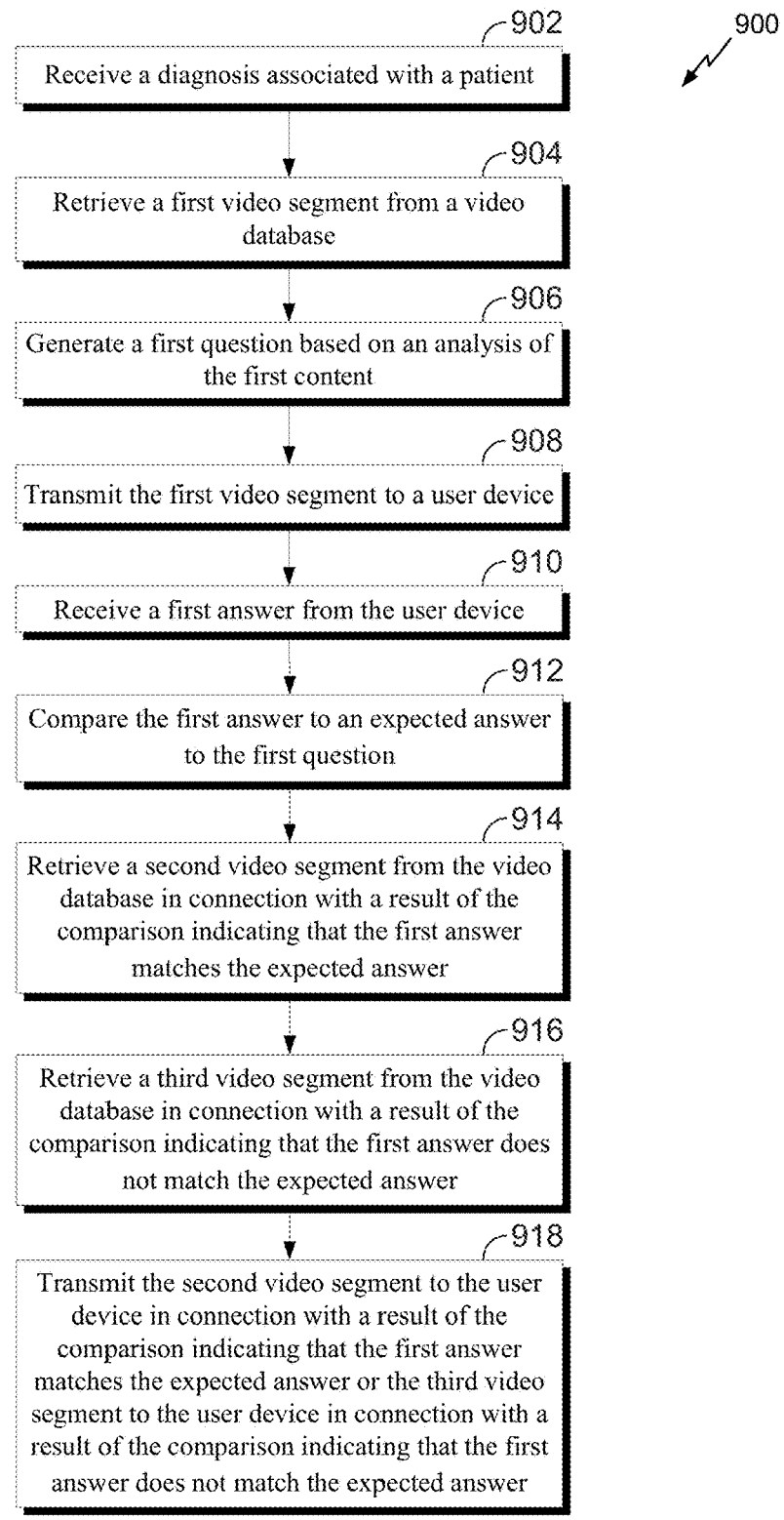
FIG. 9 is a flowchart depicting an embodiment of a process for constructing a non-linear video.

FIG. 9 is a flow diagram 900 depicting a process for constructing a non-linear video. In an embodiment, the process 900 is performed by an application executed by the Vonsent server 140 of FIG. 1. As illustrated in FIG. 9, the diagram 900 begins at block 902. At block 902, a diagnosis is received that is associated with a patient. The diagnosis can be received from an EMR system, such as the EMR system 110. At block 904, a first video segment is retrieved from a video database. In an embodiment, the first video segment comprises first content associated with a first subject.

At block 906, a first question based on an analysis of the first content is generated. The first question may test an ability of the patient to understand the first content. At block 908, the first video segment and data configured to cause a user device to display the first question is transmitted to a user device, such as the one or more user devices 150 and/or the healthcare provider device 130, over a network for presentation to the patient. At block 910, a first answer is received from the user device over the network. In an embodiment, the answer is selected by the patient in response to the first question.

At block 912, the first answer is compared to an expected answer to the first question. At block 914, a second video segment is retrieved from the video database in connection with a result of the comparison indicating that the first answer matches the expected answer. In an embodiment, the second video segment is retrieved based on the first answer and the diagnosis. In a further embodiment, the second video segment comprises second content associated with a second subject.

At block 916, a third video segment is retrieved from the video database in connection with a result of the comparison indicating that the first answer does not match the expected answer. In an embodiment, the third video segment is retrieved based on the first answer and the diagnosis. In a further embodiment, the third video segment comprises the first content and third content associated with the first subject.

At block 918, the second video segment is transmitted to the user device in connection with a result of the comparison indicating that the first answer matches the expected answer or the third video segment is transmitted to the user device in connection with a result of the comparison indicating that the first answer does not match the expected answer. The individual transmissions of the first video segment and one of the second video segment or the third video segment may reduce memory utilization on the user device from a first memory utilization level to a second memory utilization level that is lower than the first memory utilization level.

Figure 10:
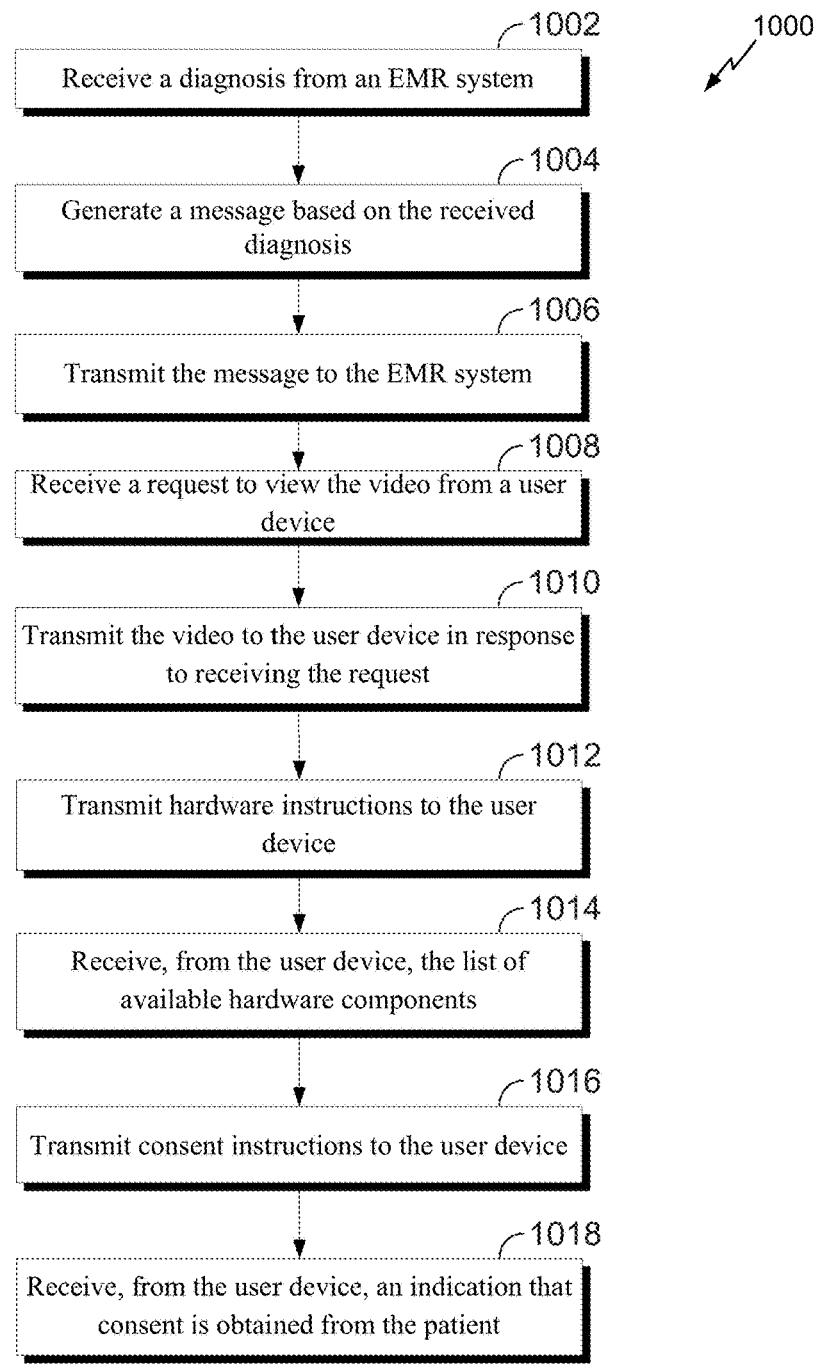
FIG. 10 is a flowchart depicting an embodiment of a process for obtaining consent from a patient.

FIG. 10 is a flowchart depicting an embodiment of a process 1000 for obtaining consent from a patient. In an embodiment, the process 1000 is performed by an application executed by the Vonsent server 140 of FIG. 1. The process 1000 begins at block 1002. At block 1002, a diagnosis is received from an EMR system, such as the EMR system 110. In an embodiment, the diagnosis is associated with a patient. For example, the diagnosis could include one or more medical codes.

At block 1004, a message based on the received diagnosis is generated. In an embodiment, the message comprises a link to a video retrieved based on the received diagnosis. In a further embodiment, the link directs the patient to a portal where the video can be directly viewed or directs the patient to a portal where the patient can log into his or her account to access the video.

At block 1006, the message is transmitted to the EMR system. At block 1008, a request to view the video from a user device is received. In an embodiment, the request is generated based on a selection of the link. In a further embodiment, the user device is the one or more user devices 150 of FIG. 1. At block 1010, the video is transmitted to the user device in response to receiving the request.

At block 1012, hardware instructions are transmitted to the user device. In an embodiment, the hardware instructions comprise a request to provide a list of available hardware components. In an embodiment, the available hardware components are those devices embedded and/or controlled by the user device that can be used to monitor a user and/or obtain consent from a user. At block 1014, the list of available hardware components is received from the user device.

At block 1016, consent instructions are transmitted to the user device. In an embodiment, the consent instructions comprise a request to obtain consent from the patient using a component in the list of available hardware components. At block 1018, an indication that consent is obtained from the patient is received from the user device. In an embodiment, the user device obtains consent from the patient by activating the component in the list of available hardware components.

Figure 11:
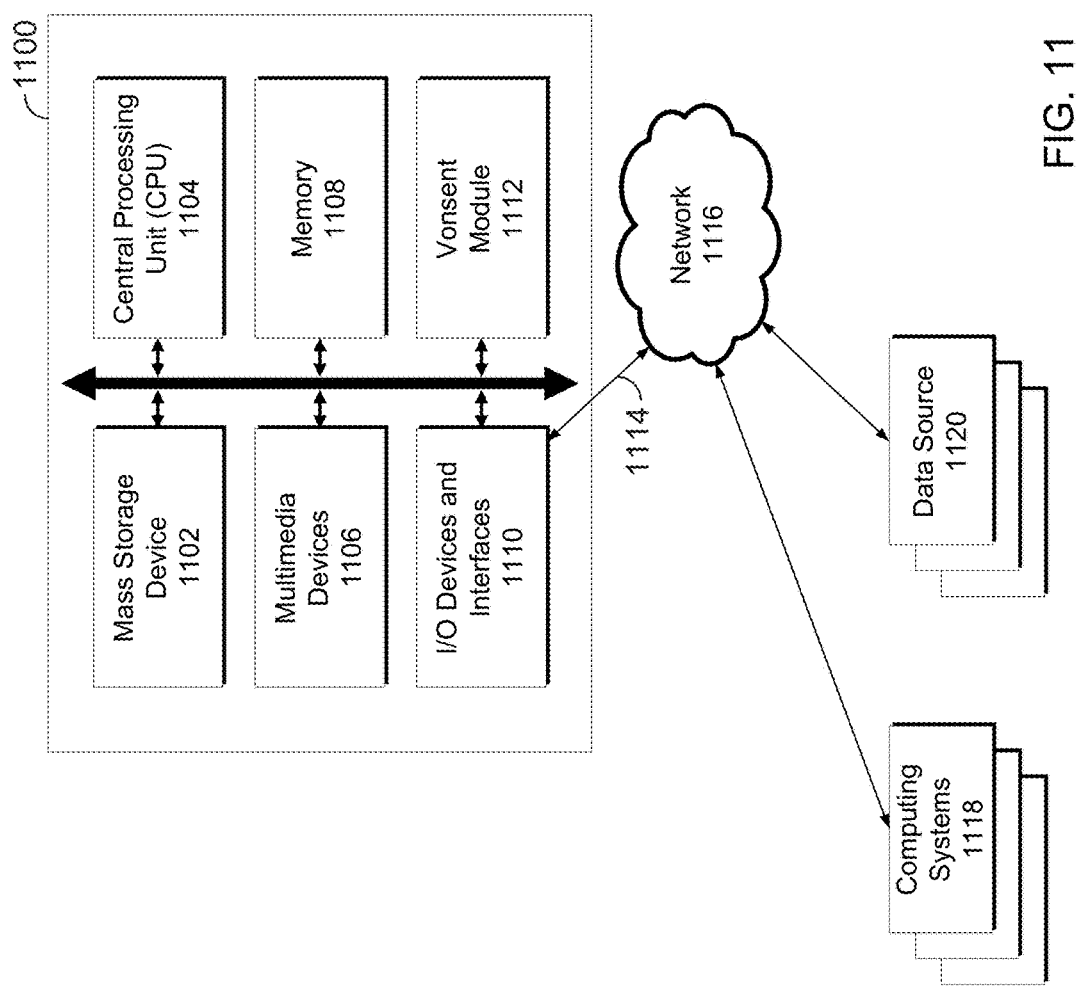
FIG. 11 is block diagram depicting an embodiment of a more detailed device of the communications system of FIG. 1.

FIG. 11 is block diagram depicting an embodiment of a more detailed device 1100 of the communications system 100 of FIG. 1. In an embodiment, the device 1100 comprises the healthcare provider device 130, the one or more user devices 150, and/or the Vonsent server 140. As illustrated in FIG. 11, the device 1100 can include a mass storage device 1102, a central processing unit (CPU) 1104, multimedia devices 1106, a memory 1108, input/output (I/O) devices and interfaces 1110, and/or a Vonsent module 1112. The Vonsent module 1112 can carry out the functions, methods, and/or processes described herein. For example, the Vonsent module 1112 can carry out the functions and processes described herein with respect to FIGS. 1-10 to present videos to patients, ensure that patients understand the content of the videos, monitor patients to ensure that they are paying attention to the videos, and/or obtain consent from the patients for a procedure or treatment. The Vonsent module 1112 is executed on the device 1100 by the CPU 1104, as described in more detail below.

In general the word "module," as used herein, refers to logic embodied in hardware or firmware or to a collection of software instructions, having entry and exit points. Modules are written in a program language, such as JAVA, JavaScript, HTML, XML, CSS, AJAX, PHP, C, C#, or C++, or the like. Software modules can be compiled or linked into an executable program, installed in a dynamic link library, or can be written in an interpreted language such as BASIC letters, ASP, PERL, LUA, PHP, Ruby, Python, or the like. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The device 1100 includes one or more CPUs 1104, which can include a microprocessor. The device 1100 further includes the memory 1108, such as random access memory (RAM) for temporary storage of information, a read only memory (ROM) for permanent storage of information, and the mass storage device 1102, such as a hard drive, a flash drive, a memory card, a diskette, an optical media storage device, or the like. Alternatively, the mass storage device 1102 can be implemented in an array of servers. Typically, the components of the device 1100 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The device 1100 includes one or more I/O devices and interfaces 1110, such as a keyboard, mouse, touchpad, and printer. The I/O devices and interfaces 1110 can include one or more display devices, such as a monitor, that allows the visual presentation of data to a user. More particularly, a display device provides for the presentation of GUIs as application software data, and multi-media presentations, for example. The I/O devices and interfaces 1110 can also provide a communications interface to various external devices. The device 1100 can include one or more multi-media devices 1106, such as speakers, video cards, graphics accelerators, microphones, and/or the like.

The device 1100 can run on a variety of computing devices, such as a server, a virtual server, a Windows server, and Structure Query Language server, a Unix Server, a Linux Server, a Mac Server, a personal computer, a laptop computer, and so forth. In other embodiments, the device 1100 can run on a mainframe computer suitable for controlling and/or communicating with large databases, performing high volume transaction processing, and generating reports from large databases. The device 1100 is generally controlled and coordinated by an operating system software, such as z/OS, Windows 95, Windows 98, Windows NT, Windows 2000, Windows XP, Windows Vista, Windows 7, Linux, Unix, BSD, SunOS, Solaris, tinyOS, iOS, Windows Mobile, Android, webOS, or other compatible operating systems, including proprietary operating systems. Operating systems control and schedule computer processes for execution, perform memory management, provide file system, networking, and I/O services, and provide a user interface, such as a graphical user interface (GUI), among other things.

The device 1100 can communicate with a network 1116 via communication link 1114 (wired, wireless, or a combination thereof). In an embodiment, the network 1116 is the network 120 of FIG. 1. The network 1116 communicates with various computing devices and/or other electronic devices. For example, the network communicates with the device 1100, computing systems 1118, and/or data source 1120. In an embodiment, the computing systems 1118 can be any of the devices or servers of the communications system 100 of FIG. 1. In a further embodiment, the data source 1120 can be any of the databases illustrated in FIG. 3. The Vonsent module 1112 can access or can be accessed through a web-enabled user access point. Connections can be a direct physical connection, a virtual connection, and other connection type. The web-enabled user access point can include a browser module that uses text, graphics, audio, video, and other media to present data and to allow interaction with data via the network 1116. The browser module can display media associated with an application as well.

The browser module or other output module can be implemented as a combination of an all-points addressable display such as a cathode ray tube (CRT), a liquid crystal display (LCD), a plasma display, a field emission display (FED), a surface-conduction electron-emitter display (SED), a light-emitting diode display (LED), an organic light-emitting diode display (OLED), an active-matrix organic light-emitting diode display (AMOLED), or other types and/or combinations of displays. The output module can be implemented to communicate with I/O devices and interfaces 1110 and they also include software with the appropriate interfaces which allow a user to access data through the use of stylized screen elements, such as menus, windows, dialogue boxes, tool bars, and controls (e.g., radio buttons, check boxes, sliding scales, and so forth). Furthermore, the output module can communicate with a set of input and output devices to receive signals from the user.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present invention herein disclosed should not be limited by the particular disclosed embodiments described above.

Conditional language, such as, among others, "can," "could," "might," or "may," unless specifically stated otherwise, or otherwise understood within the context as used, is generally intended to convey that certain embodiments include while other embodiments do not include, certain features, elements and/or blocks. Thus, such conditional language is not generally intended to imply that features, elements and/or blocks are in any way required for one or more embodiments or that one or more embodiments necessarily include logic for deciding, with or without user input or prompting, whether these features, elements and/or steps are included or are to be performed in any particular embodiment.

What is claimed is:

1. A computer-implemented method for constructing a non-linear video, comprising:

receiving a diagnosis associated with a patient from an electronic medical records system;

retrieving a first video segment from a video database based on the received diagnosis, wherein the first video segment comprises first content associated with a first subject;

generating a first question based on an analysis of the first content, wherein the first question tests an ability of the patient to understand the first content;

transmitting, over a network to a user device, a link that, when selected, causes an application executing on the user device to be redirected to a content page for accessing the first video segment;

receiving an indication of a selection of the first video segment;

transmitting, over the network to the user device, the first video segment and data configured to cause the user device to pause the first video segment during playback and display the first question;

receiving a first answer from the user device over the network, wherein the first answer is selected by the patient in response to the first question;

comparing the first answer to an expected answer to the first question;

retrieving a second video segment from the video database in connection with a result of the comparison indicating that the first answer matches the expected answer, wherein the second video segment is retrieved based on the first answer and the diagnosis, and wherein the second video segment comprises second content associated with a second subject;

retrieving a third video segment from the video database in connection with a result of the comparison indicating that the first answer does not match the expected answer, wherein the third video segment is retrieved based on the first answer and the diagnosis, and wherein the third video segment comprises the first content and third content associated with the first subject;

transmitting the second video segment to the user device in connection with a result of the comparison indicating that the first answer matches the expected answer or the third video segment to the user device in connection with a result of the comparison indicating that the first answer does not match the expected answer for presentation to the patient;

transmitting a first instruction to the user device that instructs the user device to detect, via a camera, a direction of a facial movement of the patient using a baseline point corresponding to a facial feature of the patient and, based on the detected direction of the facial movement, determine a response provided by the patient; and receiving, from the user device, an indication of the response provided by the patient.

2. The computer-implemented method of claim 1, wherein individual transmissions of the first video segment and one of the second video segment or the third video segment reduces memory utilization on the user device from a first memory utilization level to a second memory utilization level that is lower than the first memory utilization level.

3. The computer-implemented method of claim 1, wherein the result of the comparison indicates that the first answer matches the expected answer, the method further comprising:

generating a second question based on an analysis of the second content, wherein the second question tests an ability of the patient to understand the second content;

transmitting data configured to display the second question to the user device for presentation to the patient;

receiving a second answer from the user device, wherein the second answer is selected by the patient in response to the second question;

comparing the second answer to a second expected answer to the second question;

retrieving a fourth video segment from the video database in connection with a result of the comparison indicating that the second answer matches the second expected answer, wherein the fourth video segment is retrieved based on the second answer and the diagnosis, and wherein the fourth video segment comprises fourth content;

retrieving a fifth video segment from the video database in connection with a result of the comparison indicating that the second answer does not match the second expected answer, wherein the fifth video segment is retrieved based on the second answer and the diagnosis, and wherein the fifth video segment comprises the second content and fifth content; and transmitting the fourth video segment to the user device in connection with a result of the comparison indicating that the second answer matches the second expected answer or the fifth video segment to the user device in connection with a result of the comparison indicating that the second answer does not match the second expected answer for presentation to the patient.

4. The computer-implemented method of claim 1, wherein the data configured to cause the user device to pause the first video segment during playback and display the first question comprises second data that is configured to cause the user device to resume playback of the first video segment if the first answer matches the expected answer.

5. The computer-implemented method of claim 4, further comprising:

receiving an indication that the playback of the first video segment is complete; and transmitting the second video segment to the user device in connection with a result of the comparison indicating that the first answer matches the expected answer or the third video segment to the user device in connection with a result of the comparison indicating that the first answer does not match the expected answer for presentation to the patient after receiving the indication that the playback of the first video segment is complete.

6. A computer-implemented method for obtaining consent from a patient, comprising:

receiving a diagnosis from an electronic medical records system, wherein the diagnosis is associated with a patient;

generating a message based on the received diagnosis, wherein the message comprises a link to a video retrieved based on the received diagnosis;

transmitting the message to the electronic medical records system;

receiving a request to view the video from a user device, wherein the request is generated based on a selection of the link;

transmitting the video to the user device in response to receiving the request;

transmitting hardware instructions to the user device, wherein the hardware instructions comprise a request to provide a list of available hardware components;

receiving, from the user device, the list of available hardware components;

transmitting consent instructions to the user device that instruct the user device to obtain consent from the patient using a camera listed in the list of available hardware components by detecting, via the camera, a direction of a facial movement of the patient using a baseline point corresponding to a facial feature of the patient and, based on the detected direction of the facial movement, determining a response provided by the patient; and receiving, from the user device, an indication of the response provided by the patient.

7. The computer-implemented method of claim 6, further comprising storing the indication of the response provided by the patient in a consent and tracking data database.

8. The computer-implemented method of claim 7, further comprising:

receiving monitoring information collected by the user device; and storing the monitoring information in the consent and tracking data database in association with the indication of the response provided by the patient.

9. The computer-implemented method of claim 6, further comprising providing the patient with access to a social media network for interacting with other patients.

10. The computer-implemented method of claim 6, further comprising transmitting a notification to the user device that comprises at least one of a reminder regarding an appointment with a practitioner, a reminder regarding recommendations provided by the practitioner, or questions regarding a procedure that has been completed.

11. The computer-implemented method of claim 6, wherein the video comprises one of a diagnostic video, a treatment video, or a consent video.

12. The computer-implemented method of claim 6, wherein the list of available hardware components comprises at least one of the camera, a touchscreen display, a fingerprint scanner, or a microphone.

13. A computing system configured to obtain consent from a patient, the computing system comprising:
   a network interface coupled to a data network for receiving and transmitting one or more packet flows;
   a computer processor; and
   a computer readable storage medium storing program instructions configured for execution by the computer processor in order to cause the computing system to:
      receive a diagnosis from an electronic medical records system, wherein the diagnosis is associated with a patient;
      generate a message based on the received diagnosis, wherein the message comprises a link to a video retrieved based on the received diagnosis;
      transmit the message to the electronic medical records system;
      receive a request to view the video from a user device, wherein the request is generated based on a selection of the link;
      transmit the video to the user device in response to receiving the request;
      generate hardware instructions that are transmitted to the user device, wherein the hardware instructions comprise a request to provide a list of available hardware components;
      receive, from the user device, the list of available hardware components;
      transmit consent instructions to the user device, wherein the consent instructions comprise a request to obtain consent from the patient using a camera listed in the list of available hardware components, wherein the consent instructions cause the user device to detect, via the camera, a direction of a facial movement of the patient using a baseline point corresponding to a facial feature of the patient and, based on the detected direction of the facial movement, determine a response provided by the patient; and
      receive, from the user device, an indication that consent is obtained from the patient.

14. The computing system of claim 13, wherein the program instructions are further configured to cause the computing system to store the indication that consent is obtained in a consent and tracking data database.

15. The computing system of claim 14, wherein the program instructions are further configured to cause the computing system to:
   receive monitoring information collected by the user device; and
   store the monitoring information in the consent and tracking data database in association with the indication that consent is obtained.

16. The computing system of claim 13, wherein the program instructions are further configured to cause the computing system to provide the patient with access to a social media network for interacting with other patients.

17. The computing system of claim 13, wherein the program instructions are further configured to cause the computing system to transmit a notification to the user device that comprises at least one of a reminder regarding an appointment with a practitioner, a reminder regarding recommendations provided by the practitioner, or questions regarding a procedure that has been completed.

18. The computing system of claim 13, wherein the video comprises one of a diagnostic video, a treatment video, or a consent video.

19. The computing system of claim 13, wherein the list of available hardware components comprises at least one of the camera, a touchscreen display, a fingerprint scanner, or a microphone.

* * * * *